US008795701B2

(12) United States Patent
Andersch et al.

(10) Patent No.: US 8,795,701 B2
(45) Date of Patent: Aug. 5, 2014

(54) METHOD FOR BETTER UTILIZING THE PRODUCTION POTENTIAL OF TRANSGENIC PLANTS

(75) Inventors: Wolfram Andersch, Bergisch Gladbach (DE); Christian Funke, Leichlingen (DE); Heike Hungenberg, Langenfeld (DE); Wolfgang Thielert, Odenthal (DE)

(73) Assignee: Bayer CropScience AG, Monheim (DE)

( * ) Notice: Subject to any disclaimer, the term of this patent is extended or adjusted under 35 U.S.C. 154(b) by 446 days.

(21) Appl. No.: 12/596,201

(22) PCT Filed: Apr. 8, 2008

(86) PCT No.: PCT/EP2008/002759
§ 371 (c)(1), (2), (4) Date: Oct. 16, 2009

(87) PCT Pub. No.: WO2008/125245
PCT Pub. Date: Oct. 23, 2008

(65) Prior Publication Data

US 2010/0130366 A1 May 27, 2010

(30) Foreign Application Priority Data

Apr. 17, 2007 (DE) ......................... 10 2007 018 452

(51) Int. Cl.

| | |
|---|---|
| ***A01N 43/92*** | (2006.01) |
| *A01N 33/06* | (2006.01) |
| *A01N 43/56* | (2006.01) |
| *A61K 31/44* | (2006.01) |
| *A61K 31/205* | (2006.01) |

(52) U.S. Cl.
USPC ........... 424/405; 424/489; 504/118; 504/129; 504/130; 504/134; 504/139; 504/140; 504/141; 504/149; 514/183; 514/229.2; 514/245; 514/277; 514/341; 514/342; 514/352; 514/353; 514/357; 514/365; 514/370; 514/406

(58) Field of Classification Search
USPC ......... 504/118, 129, 130, 134, 139, 140, 141, 504/149; 514/183, 229.2, 245, 277, 336, 514/341, 342, 352, 353, 357, 365, 370, 514/406; 424/405, 489
See application file for complete search history.

(56) References Cited

U.S. PATENT DOCUMENTS

| | | | | |
|---|---|---|---|---|
| 7,696,233 | B2 * | 4/2010 | Lahm et al. | 514/341 |
| 2005/0274059 | A1 * | 12/2005 | Angst et al. | 43/124 |
| 2007/0232598 | A1 | 10/2007 | Funke et al. | |
| 2007/0244073 | A1 | 10/2007 | Angst et al. | |
| 2008/0027046 | A1 | 1/2008 | Annan et al. | |
| 2009/0104145 | A1 | 4/2009 | Hughes et al. | |
| 2010/0105557 | A1 * | 4/2010 | Habicher et al. | 504/113 |
| 2010/0130561 | A1 * | 5/2010 | Andersch et al. | 514/341 |

FOREIGN PATENT DOCUMENTS

| | | | | |
|---|---|---|---|---|
| WO | WO2006/007595 | A2 * | 1/2006 | A01N 43/56 |
| WO | WO2006007595 | A2 * | 1/2006 | A01N 43/56 |

OTHER PUBLICATIONS

International Search Report PCT/EP2008/002759; May 29, 2008 (6 pages).

* cited by examiner

*Primary Examiner* — Jane C Oswecki
(74) *Attorney, Agent, or Firm* — Miles & Stockbridge, P.C.

(57) ABSTRACT

The invention relates to a method for improving the utilization of the production potential of transgenic plants which comprises treating the plant with active compound combinations comprising an active compound from the group of the anthranilamides and at least one further insecticide.

18 Claims, No Drawings

METHOD FOR BETTER UTILIZING THE PRODUCTION POTENTIAL OF TRANSGENIC PLANTS

CROSS REFERENCE TO RELATED APPLICATIONS

This application is a §371 National Stage Application of PCT/EP2008/002759 filed Apr. 8, 2008, which claims priority to German Application 10 2007 018 452.4 filed Apr. 17, 2007.

BACKGROUND OF THE INVENTION

1. Field of the Invention

The invention relates to a method for improving the utilization of the production potential of transgenic plants.

2. Description of Related Art

In recent years, there has been a marked increase in the proportion of transgenic plants in agriculture, even if regional differences are still noticeable to date. Thus, for example, the proportion of transgenic maize in the USA has doubled from 26% to 52% since 2001, while transgenic maize has hardly been of any practical importance in Germany. However, in other European countries, for example in Spain, the proportion of transgenic maize is already about 12%.

Transgenic plants are employed mainly to utilize the production potential of respective plant varieties in the most favourable manner, at the lowest possible input of production means. The aim of the genetic modification of the plants is in particular the generation of resistance in the plants to certain pests or harmful organisms or else herbicides and also to abiotic stress (for example drought, heat or elevated salt levels). It is also possible to modify a plant genetically to increase certain quality or product features, such as, for example, the content of selected vitamins or oils, or to improve certain fibre properties.

Herbicide resistance or tolerance can be achieved, for example, by incorporating genes into the useful plant for expressing enzymes to detoxify certain herbicides, so that a relatively unimpeded growth of these plants is possible even in the presence of these herbicides for controlling broad-leaved weeds and weed grasses. Examples which may be mentioned are cotton varieties or maize varieties which tolerate the herbicidally active compound glyphosate (Roundup®), (Roundup Ready®, Monsanto) or the herbicides glufosinate or oxynil.

More recently, there has also been the development of useful plants comprising two or more genetic modifications ("stacked transgenic plants" or multiply transgenic crops). Thus, for example, Monsanto has developed multiply transgenic maize varieties which are resistant to the European corn borer (*Ostrinia nubilalis*) and the Western corn rootworm (*Diabrotica virgifera*). Also known are maize and cotton crops which are both resistant to the Western corn rootworm and the cotton bollworm and tolerant to the herbicide Roundup®.

SUMMARY OF THE INVENTION

It has now been found that the utilization of the production potential of transgenic useful plants can be improved even more by treating the plants with a mixture of an active compound of the formula (I) and an active compound of group II. Here, the term "treatment" includes all measures resulting in a contact between these active compounds and at least one plant part. "Plant parts" are to be understood as meaning all above-ground and below-ground parts and organs of plants, such as shoot, leaf, flower and root, by way of example leaves, needles, stalks, stems, flowers, fruit bodies, fruits and seed, and also roots, tubers and rhizomes. The plant parts also include harvested material and also vegetative and generative propagation material, for example cuttings, tubers, rhizomes, slips and seed.

It is already known that compounds of the formula (I) have insecticidal action (for example from WO 03/015519 and WO 04/067528), and that they can be used in mixtures (for example from WO 05/048711, WO 05/107468, WO 06/007595, WO 06/068669). These documents are expressly incorporated herein by way of reference.

The mixtures which can be used according to the invention comprise an active compound of the formula (I) as follows:

(I)

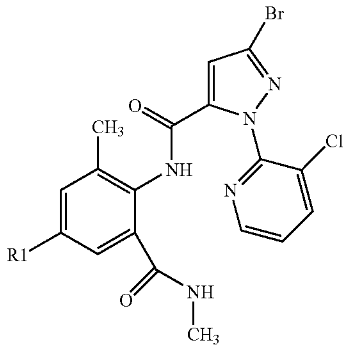

where

R1 represents Cl or cyano and at least one compound of group II, which comprises imidachloprid, thiodicarb, clothianidin, methiocarb, thiacloprid, thiamethoxam, fipronil, tefluthrin, beta-cyfluthrin, abamectin or spinosad.

DETAILED DESCRIPTION OF A PREFERRED EMBODIMENT

Preference is given to mixtures comprising the active compound of the formula (I-1)

(I-1)

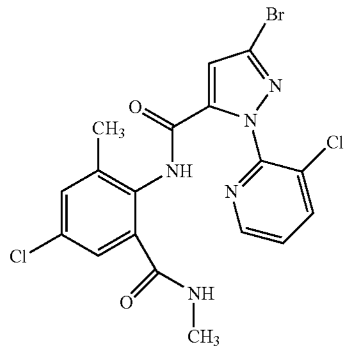

and at least one compound of group II, which comprises imidachloprid, thiodicarb, clothianidin, methiocarb, thiacloprid, thiamethoxam, fipronil, tefluthrin, beta-cyfluthrin, abamectin or spinosad.

Preference is likewise given to mixtures comprising the active compound of the formula (I-2)

(I-2)

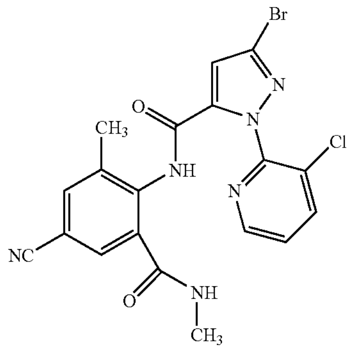

and at least one compound of group II, which comprises imidachloprid, thiodicarb, clothianidin, methiocarb, thiacloprid, thiamethoxam, fipronil, tefluthrin, beta-cyfluthrin, abamectin or spinosad.

Particular preference is given to the mixtures below comprising the active compound of the formula I-1 and imidacloprid;
the active compound of the formula I-1 and clothianidin;
the active compound of the formula I-2 and imidacloprid;
the active compound of the formula I-2 and clothianidin.

In addition, the active compound combinations may also comprise further fungicidally, acaricidally or insecticidally active co-components.

In general, the mixtures according to the invention comprise an active compound of the formula (I) and an active compound of group (II) in the stated preferred and particularly preferred mixing ratios:

The preferred mixing ratio is from 250:1 to 1:50.

The particularly preferred mixing ratio is from 25:1 to 1:25.

The mixing ratios are based on weight ratios. The ratio is to be understood as active compound of the formula (I):co-component of group (II).

According to the method proposed according to the invention, transgenic plants, in particular useful plants, are treated with the mixtures according to the invention to increase agricultural productivity. For the purpose of the invention, transgenic plants are plants which contain at least one "foreign gene". The term "foreign gene" in this connection means a gene or gene fragment which may originate or be derived from another plant of the same species, from plants of a different species, but also from organisms from the animal kingdom or microorganisms (including viruses) ("foreign gene") and/or, if appropriate, already has mutations compared to a naturally occurring gene or gene fragment. According to the invention, it is also possible to use synthetic genes or gene fragments, which is also included in the term "foreign gene" here. It is also possible for a transgenic plant to code for two or more foreign genes of different origin.

For the purpose of the invention, the "foreign gene" is further characterized in that it comprises a nucleic acid sequence which has a certain biological or chemical function or activity in the transgenic plant. In general, these genes code for biocatalysts, such as, for example, enzymes or ribozymes, or else they comprise regulatory sequences, such as, for example, promoters or terminators, for controlling the expression of endogenous proteins. However, to this end, they may also code for regulatory proteins, such as, for example, repressors or inductors. Furthermore, the foreign gene may also serve the targeted localization of a gene product of the transgenic plant, coding, for example, for a signal peptide. The foreign gene may also code for inhibitors, such as, for example, antisense RNA.

The person skilled in the art is readily familiar with numerous different methods for producing transgenic plants and methods for the targeted mutagenesis, for gene transformation and cloning, for example from: Willmitzer, 1993, Transgenic plants, in: Biotechnology, A Multivolume Comprehensive Treatise, Rehm et al. (eds.), Vol. 2, 627-659, VCH Weinheim, Germany; McCormick et al., 1986, Plant Cell Reports 5: 81-84; EP-A 0221044; EP-A 0131624, or Sambrook et al., 1989, "Molecular Cloning: A Laboratory Manual", 3rd Ed., Cold Spring Harbor Laboratory Press, Cold Spring Harbor, N.Y.; Winnacker, 1996, "Gene und Klone" [Genes and Clones], 2nd Ed., VCH Weinheim or Christou, 1996, Trends in Plant Science 1: 423-431. Examples of transit or signal peptides or time- or site-specific promoters are disclosed, for example, in Braun et al., 1992, EMBO J. 11: 3219-3227; Wolter et al., 1988, Proc. Natl. Acad. Sci. USA 85: 846-850; Sonnewald et al., 1991, Plant J. 1: 95-106.

A good example of a complex genetic manipulation of a useful plant is the so-called GURT technology ("Genetic Use Restriction Technologies") which allows the technical control of the propagation of the transgenic plant variety in question. To this end, in general two or three foreign genes are cloned into the useful plant which, in a complex interaction after administration of an external stimulus, trigger a cascade resulting in the death of the embryo which would otherwise develop. To this end, the external stimulus (for example an active compound or another chemical or abiotic stimulus) may interact, for example, with a repressor which then no longer suppresses the expression of a recombinase, so that the recombinase is able to cleave an inhibitor thus allowing expression of a toxin causing the embryo to die. Examples of this type of transgenic plants are disclosed in U.S. Pat. No. 5,723,765 or U.S. Pat. No. 5,808,034.

Accordingly, the person skilled in the art is familiar with processes for generating transgenic plants which, by virtue of the integration of regulatory foreign genes and the overexpression, suppression or inhibition of endogenous genes or gene sequences mediated in this manner, if appropriate, or by virtue of the existence or expression of foreign genes or fragments thereof, have modified properties.

As already discussed above, the method according to the invention allows better utilization of the production potential of transgenic plants. On the one hand, this may, if appropriate, be based on the fact that the application rate of the active compound which can be employed according to the invention can be reduced, for example by lowering the dose employed or else by reducing the number of applications. On the other hand, if appropriate, the yield of the useful plants may be increased quantitatively and/or qualitatively. This is true in particular in the case of a transgenically generated resistance to biotic or abiotic stress.

Depending on the plant species or plant varieties, their location and the growth conditions (soils, climate, vegetation period, nutrients), these synergistic actions may vary and may be multifarious. Thus possible are, for example, reduced application rates and/or a widening of the activity spectrum and/or an increase of the activity of the compounds and compositions used according to the invention, better plant growth, increased tolerance to high or low temperatures, increased tolerance to drought or to water or soil salt content, increased flowering, easier harvesting, accelerated maturation, higher harvest yields, higher quality and/or higher nutrient value of the harvested products, increased storability and/or processability of the harvested products, which exceed the effects normally to be expected.

These advantages are the result of a synergistic action, achieved according to the invention, between the mixtures according to the invention which can be employed and the respective principle of action of the genetic modification of the transgenic plant. This reduction of production means as a result of the synergism, with simultaneous yield or quality increase, is associated with considerable economical and ecological advantages.

A list of examples known to the person skilled in the art of transgenic plants, with the respective affected structure in the plant or the protein expressed by the genetic modification in the plant being mentioned, is compiled in Table 1. Here, the structure in question or the principle expressed is in each case grouped with a certain feature in the sense of a tolerance to a certain stress factor. A similar list (Table 3) compiles—in a slightly different arrangement—likewise examples of principles of action, tolerances induced thereby and possible useful plants. Further examples of transgenic plants suitable for the treatment according to the invention are compiled in Table 4.

In an advantageous embodiment, the mixtures according to the invention are used for treating transgenic plants comprising at least one foreign gene coding for a Bt toxin. A Bt toxin is a protein originating from or derived from the soil bacterium *Bacillus thuringiensis* which either belongs to the group of the crystal toxins (Cry) or the cytolytic toxins (Cyt). In the bacterium, they are originally formed as protoxins and are only metabolized in alkaline medium—for example in the digestive tract of certain feed insects—to their active form. There, the active toxin then binds to certain hydrocarbon structures at cell surfaces causing pores to be formed which destroy the osmotic potential of the cell, which may effect cell lysis. The result is the death of the insects. Bt toxins are active in particular against certain harmful species from the orders of the Lepidoptera (butterflies), Homoptera, Diptera and Coleoptera (beetles) in all their development stages; i.e. from the egg larva via their juvenile forms to their adult forms.

It has been known for a long time that gene sequences coding for Bt toxins, parts thereof or else peptides or proteins derived from Bt toxins can be cloned with the aid of genetic engineering into agriculturally useful plants to generate transgenic plants having endogenous resistance to pests sensitive to Bt toxins. For the purpose of the invention, the transgenic plants coding for at least one Bt toxin or proteins derived therefrom are defined as "Bt plants".

The "first generation" of such Bt plants generally only comprise the genes enabling the formation of a certain toxin, thus only providing resistance to one group of pathogens. An example of a commercially available maize variety comprising the gene for forming the Cry1Ab toxin is "YieldGard®" from Monsanto which is resistant to the European corn borer. In contrast, in the Bt cotton variety (Bollgard®), resistance to other pathogens from the family of the Lepidoptera is generated by introduction by cloning of the genes for forming the Cry1Ac toxin. Other transgenic crop plants, in turn, express genes for forming Bt toxins with activity against pathogens from the order of the Coleoptera. Examples that may be mentioned are the Bt potato variety "NewLeaf®" (Monsanto) capable of forming the Cry3A toxin, which is thus resistant to the Colorado potato beetle, and the transgenic maize variety "YieldGard®" (Monsanto) which is capable of forming the Cry 3Bb1 toxin and is thus protected against various species of the Western corn rootworm.

In a "second generation", the multiply transgenic plants, already described above, expressing or comprising at least two foreign genes were generated.

Preference according to the invention is given to transgenic plants with Bt toxins from the group of the Cry family (see, for example, Crickmore et al., 1998, Microbiol. Mol. Biol. Rev. 62: 807-812), which are particularly effective against Lepidoptera, Coleoptera and Diptera. Examples of genes coding for the proteins are:

cry1Aa1, cry1Aa2, cry1Aa3, cry1Aa4, cry1Aa5, cry1Aa6, cry1Aa7, cry1Aa8, cry1Aa9, cry1Aa10, cry1Aa11 cry1Ab1, cry1Ab2, cry1Ab3, cry1Ab4, cry1Ab5, cry1Ab6, cry1Ab7, cry1Ab8, cry1Ab9, cry1Ab10, cry1Ab11, cry1Ab12, cry1Ab13, cry1Ab14, cry1Ac1, cry1Ac2, cry1Ac3, cry1Ac4, cry1Ac5, cry1Ac6, cry1Ac7, cry1Ac8, cry1Ac9, cry1Ac10, cry1Ac11, cry1Ac12, cry1Ac13, cry1Ad1, cry1Ad2, cry1Ae1, cry1Af1, cry1Ag1, cry1Ba1, cry1Ba2, cry1Bb1, cry1Bc1, cry1Bd1, cry1Be1, cry1Ca1, cry1Ca2, cry1Ca3, cry1Ca4, cry1Ca5, cry1Ca6, cry1Ca7, cry1Cb1, cry1Cb2, cry1Da1, cry1Da2, cry1Db1, cry1Ea1, cry1Ea2, cry1Ea3, cry1Ea4, cry1Ea5, cry1Ea6, cry1Eb1, cry1Fa1, cry1Fa2, cry1Fb1, cry1Fb2, cry1Fb3, cry1Fb4, cry1Ga1, cry1Ga2, cry1Gb1, cry1Gb2, cry1Ha1, cry1Hb1, cry1Ia1, cry1Ia2, cry1Ia3, cry1Ia4, cry1Ia5, cry1Ia6, cry1Ib1, cry1Ic1, cry1Id1, cry1Ie1, cry1I-like, cry1Ja1, cry1Jb1, cry1Jc1, cry1Ka1, cry1-like, cry2Aa1, cry2Aa2, cry2Aa3, cry2Aa4, cry2Aa5, cry2Aa6, cry2Aa7, cry2Aa8, cry2Aa9, cry2Ab1, cry2Ab2, cry2Ab3, cry2Ac1, cry2Ac2, cry2Ad1, cry3Aa1, cry3Aa2, cry3Aa3, cry3Aa4, cry3Aa5, cry3Aa6, cry3Aa7, cry3Ba1, cry3Ba2, cry3Bb1, cry3Bb2, cry3Bb3, cry3Ca1, cry4Aa1, cry4Aa2, cry4Ba1, cry4Ba2, cry4Ba3, cry4Ba4, cry5Aa1, cry5Ab1, cry5Ac1, cry5Ba1, cry6Aa1, cry6Ba1, cry7Aa1, cry7Ab1, cry7Ab2, cry8Aa1, cry8Ba1, cry8Ca1, cry9Aa1, cry9Aa2, cry9Ba1, cry9Ca1, cry9Da1, cry9Da2, cry9Ea1, cry9 like, cry10Aa1, cry10Aa2, cry11Aa1, cry11Aa2, cry11Ba1, cry11Bb1, cry12Aa1, cry13Aa1, cry14Aa1, cry15Aa1, cry16Aa1, cry17Aa1, cry18Aa1, cry18Ba1, cry18Ca1, cry19Aa1, cry19Ba1, cry20Aa1, cry21Aa1, cry21Aa2, cry22Aa1, cry23Aa1, cry24Aa1, cry25Aa1, cry26Aa1, cry27Aa1, cry28Aa1, cry28Aa2, cry29Aa1, cry30Aa1, cry31Aa1, cyt1Aa1, cyt1Aa2, cyt1Aa3, cyt1Aa4, cyt1Ab1, cyt1Ba1, cyt2Aa1, cyt2Ba1, cyt2Ba2, cyt2Ba3, cyt2Ba4, cyt2Ba5, cyt2Ba6, cyt2Ba7, cyt2Ba8, cyt2Bb1.

Particular preference is given to the genes or gene sections of the subfamilies cry1, cry2, cry3, cry5 and cry9; especially preferred are cry1Ab, cry1Ac, cry3A, cry3B and cry9C.

Furthermore, it is preferred to use plants which, in addition to the genes for one or more Bt toxins, express or contain, if appropriate, also genes for expressing, for example, a protease or peptidase inhibitor (such as in WO-A 95/35031), of herbicide resistances (for example to glufosinate or glyphosate by expression of the pat gene or bar gene) or for becoming resistant to nematodes, fungi or viruses (for example by expressing a gluconase, chitinase). However, they may also be modified in their metabolic properties, so that they show a qualitative and/or quantitative change of ingredients (for example by modification of the energy, carbohydrate, fatty acid or nitrogen metabolism or by metabolite currents influencing these (see above).

A list of examples of principles of action which can be introduced by genetic modification into a useful plant and which are suitable for the treatment according to the invention on their own or in combination is compiled in Table 2. Under the header "AP" (active principle), this table contains the respective principle of action and associated therewith the pest to be controlled.

In a particularly preferred variant, the process according to the invention is used for treating transgenic vegetable, maize, soya bean, cotton, tobacco, rice, potato and sugar beet varieties. These are preferably Bt plants.

The vegetable plants or varieties are, for example, the following useful plants:

potatoes: preferably starch potatoes, sweet potatoes and table potatoes;

root vegetables: preferably carrots, turnips (swedes, stubble turnips (*Brassica rapa* var. *rapa*), spring turnips, autumn turnips (*Brassica campestris* ssp. *rapifera*), *Brassica rapa* L. ssp. *rapa f. teltowiensis*), scorzonera, Jerusalem artichoke, turnip-rooted parsley, parsnip, radish and horseradish;

tuber vegetables: preferably kohlrabi, beetroot, celeriac, garden radish;

bulb crops: preferably scallion, leek and onions (planting onions and seed onions);

*brassica* vegetables: preferably headed cabbage (white cabbage, red cabbage, kale, savoy cabbage), cauliflowers, broccoli, curly kale, marrow-stem kale, seakale and Brussels sprouts;

fruiting vegetables: preferably tomatoes (outdoor tomatoes, vine-ripened tomatoes, beef tomatoes, greenhouse tomatoes, cocktail tomatoes, industrial and fresh market tomatoes), melons, eggplants, aubergines, pepper (sweet pepper and hot pepper, Spanish pepper), chilli pepper, pumpkins, courgettes and cucumbers (outdoor cucumbers, greenhouse cucumbers snake gourds and gherkins);

vegetable pulses: preferably bush beans (as sword beans, string beans, flageolet beans, wax beans, corn beans of green- and yellow-podded cultivars), pole beans (as sword beans, string beans, flageolet beans, wax beans of green-, blue- and yellow-podded cultivars), broadbeans (field beans, Windsor beans, cultivars having white- and black-spotted flowers), peas (chickling vetch, chick-peas, marrow peas, shelling peas, sugar-peas, smooth peas, cultivars having light- and dark-green fresh fruits) and lentils;

green vegetables and stem vegetables: preferably Chinese cabbage, round-headed garden lettuce, curled lettuce, lamb's-lettuce, iceberg lettuce, romaine lettuce, oakleaf lettuce, endives, radicchio, lollo rossa, ruccola lettuce, chicory, spinach, chard (leaf chard and stem chard) and parsley;

other vegetables: preferably asparagus, rhubarb, chives, artichokes, mint varieties, sunflowers, Florence fennel, dill, garden cress, mustard, poppy seed, peanuts, sesame and salad chicory.

Bt vegetables including exemplary methods for preparing them are described in detail, for example, in Barton et al., 1987, Plant Physiol. 85: 1103-1109; Vaeck et al., 1987, Nature 328: 33-37; Fischhoff et al., 1987, Bio/Technology 5: 807-813. In addition, Bt vegetable plants are already known as commercial varieties, for example the potato cultivar NewLeaf® (Monsanto). The preparation of Bt vegetables is also described in U.S. Pat. No. 6,072,105.

Likewise, Bt cotton is already known in principle, for example from U.S. Pat. No. 5,322,938 or from Prietro-Samsonór et al., J. Ind. Microbiol. & Biotechn. 1997, 19, 202, and H. Agaisse and D. Lereclus, J. Bacteriol. 1996, 177, 6027. Different varieties of Bt cotton, too, are already commercially available, for example under the name NuCOTN® (Deltapine (USA)). In the context of the present invention, particular preference is given to Bt cotton NuCOTN33® and NuCOTN33B®.

The use and preparation of Bt maize has likewise already been known for a long time, for example from Ishida, Y., Saito, H., Ohta, S., Hiei, Y., Komari, T., and Kumashiro, T. (1996). High efficiency transformation of maize (*Zea mayz* L.) mediated by *Agrobacterium tumefaciens*. Nature Biotechnology 4: 745-750. EP-B-0485506, too, describes the preparation of Bt maize plants. Furthermore, different varieties of Bt maize are commercially available, for example under the following names (company/companies is/are in each case given in brackets): KnockOut® (Novartis Seeds), NaturGard® (Mycogen Seeds), Yieldgard® (Novartis Seeds, Monsanto, Cargill, Golden Harvest, Pioneer, DeKalb inter alia), Bt-Xtra® (DeKalb) and StarLink® (Aventis CropScience, Garst inter alia). For the purpose of the present invention, particular preference is given especially to the following maize cultivars: KnockOut®, NaturGard®, Yieldgard®, Bt-Xtra® and StarLink®.

For soya beans, too, Roundup®Ready cultivar or cultivars resistant to the herbicide Liberty Link® are available and can be treated according to the invention. In the case of rice, a large number of "Golden Rice" lines are available which are likewise characterized in that, by virtue of a transgenic modification, they have an increased content of provitamin A. They, too, are examples of plants which can be treated by the method according to the invention, with the advantages described.

The method according to the invention is suitable for controlling a large number of harmful organisms which occur in particular in vegetables, maize and cotton, preferably arthropods and nematodes, in particular insects and arachnids. The pests mentioned include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis*

*gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The method according to the invention is particularly suitable for treating sugar beet or Bt vegetables, Bt maize, Bt cotton, Bt soya beans, Bt tobacco and also Bt rice or Bt potatoes for controlling insects from the order of the Isoptera, for example, *Reticulitermes* spp., from the order of the Thysanoptera, for example, *Thrips tabaci, Thrips palmi, Frankliniella occidentalis*, from the order of the Heteroptera, for example, *Eurygaster* spp., *Dysdercus intermedius, Piesma quadrata*, from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Phylloxera vastatrix, Pemphigus* spp., *Macrosiphum avenae, Myzus* spp., *Phorodon humuli, Rhopa-losiphum padi, Empoasca* spp., *Nephotettix cincticeps, Lecanium corni, Saissetia oleae, Laodelphax striatellus, Nilaparvata lugens, Aonidiella aurantii, Pseudococcus* spp., *Psylla* spp., from the order of the Lepidoptera, for example, *Pectinophora gossypiella, Chematobia brumata, Lithocolletis blancardella, Hyponomeuta padella, Plutella xylostella, Euproctis chrysorrhoea, Lymantria* spp., *Phyllocnistis citrella, Agrotis* spp., *Earias insulana, Heliothis* spp., *Mamestra brassicae, Spodoptera* spp., *Trichoplusia ni, Carpocapsa pomonella, Pieris* spp., *Chilo* spp., *Pyrausta nubilalis, Ephestia kuehniella, Capua reticulana, Clysia ambiguella, Tortrix viridana, Cnaphalocerus* spp., *Oulema oryzae*, from the order of the Coleoptera, for example, *Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Meligethes aeneus, Tribolium* spp., *Tenebrio molitor, Agriotes* spp., *Lissorhoptrus oryzophilus*, from the order of the Hymenoptera, for example, *Diprion* spp., *Hoplocampa* spp. or from the order of the Diptera, for example, *Oscinella frit, Phorbia* spp., *Pegomyia hyoscyami, Ceratitis capitata, Dacus oleae, Hylemyia* spp., *Liriomyza* spp.

The active compound combinations can be employed in customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are prepared in a known manner, for example by mixing the active compounds with extenders, i.e. liquid solvents and/or solid carriers, if appropriate using surfactants, i.e. emulsifiers and/or dispersants and/or foam-formers. The formulations are prepared either in suitable plants or else before or during application.

Wettable powders are preparations which can be dispersed homogeneously in water and which, in addition to the active compound and beside a diluent or inert substance, also comprise wetting agents, for example polyethoxylated alkylphenols, polyethoxylated fatty alcohols, alkylsulphonates or alkylphenylsulphonates and dispersants, for example sodium lignosulphonate, sodium 2,2'-dinaphthylmethane-6,6'-disulphonate.

Dusts are obtained by grinding the active compound with finely distributed solid substances, for example talc, natural clays, such as kaolin, bentonite, pyrophillite or diatomaceous earth. Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

These individual types of formulation are known in principle and are described, for example, in: Winnacker-Küchler, 1986, "Chemische Technologie" [Chemical Technology], Volume 7, 4th Ed., C. Hauser Verlag Munich; van Falkenberg, 1972-73, "Pesticides Formulations", 2nd Ed., Marcel Dekker N.Y.; Martens, 1979, "Spray Drying Handbook", 3rd Ed., G. Goodwin Ltd. London.

Based on his general expert knowledge, the person skilled in the art is able to choose suitable formulation auxiliaries (in this context, see, for example, Watkins, "Handbook of Insecticide Dust Diluents and Carriers", 2nd Ed., Darland Books, Caldwell N.J.; v. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood, N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1967; Winnacker-Küchler, "Chemische Technologie" [Chemical Technology], Volume 7, 4th Ed., C. Hanser Verlag Munich 1986.

The active compound combinations according to the invention, in commercially available formulations and in the use forms prepared from these formulations, can be present in a mixture with other known active compounds such as insecticides, attractants, sterilants, bactericides, acaricides, nematicides, fungicides, growth regulators or herbicides. The insecticides include, for example, phosphoric esters, carbamates, carboxylic esters, chlorinated hydrocarbons, phenylureas, substances produced by microorganisms, and the like.

A mixture with other known active compounds such as herbicides, or with fertilizers and growth regulators, is also possible.

When used as insecticides, the active compound combinations according to the invention in their commercially available formulations and in the use forms which are prepared from these formulations may furthermore be present as a mixture with synergists. Synergists are compounds by which the action of the active compounds is increased without it being necessary for the synergist added to be active itself.

In general, the formulations comprise from 0.01 to 98% by weight of active compound, preferably from 0.5 to 90%. In wettable powders, the active compound concentration is, for example, from about 10 to 90% by weight, the remainder to 100% by weight consisting of customary formulation components. In the case of emulsifiable concentrates, the active compound concentration can be from about 5 to 80% by weight. In most cases, formulations in the form of dusts comprise from 5 to 20% by weight of active compound, sprayable solutions comprise about 2 to 20% by weight. In the case of granules, the active compound content depends partially on whether the active compound is present in liquid or solid form and on which granulation auxiliaries, fillers, etc., are used.

The required application rate may also vary with external conditions such as, inter alia, temperature and humidity. It may vary within wide limits, for example between 0.1 g/h and 5.0 kg/ha or more of active substance. Owing to the synergistic effects between Bt vegetables and the active compound combinations according to the invention, particular preference is given to application rates of from 0.1 to 500 g/ha. Particular preference is given to application rates of from 10 to 500 g/ha, especially preferred are 10 to 200 g/ha.

In their commercial formulations and in the use forms prepared from these formulations, the mixtures according to the invention may be present as mixtures with other active compounds, such as insecticides, attractants, sterilants, acaricides, nematicides, fungicides, growth-regulating substances or herbicides.

The active compound content of the use forms prepared from the commercial formulations may vary within wide limits. The active compound concentration of the use forms may be from 0.0000001 to 95% by weight of active compound and is, preferably between 0.0001 and 1% by weight.

TABLE 1

| Plant: Maize | |
|---|---|
| Structure affected or principle expressed | Feature of the plant/tolerance to |
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acid, cyclohexanedione |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazole, pyridine derivative, phenopylate, oxadiazoles etc. |
| cytochrome P450 e.g. P450 SU1 | xenobiotics and herbicides, such as sulphonylurea |
| dimboa biosynthesis (Bx1-Gen) | *Helminthosporium turcicum*, *Rhopalosiphum maydis*, *Diplodia maydis*, *Ostrinia nubilalis*, Lepidoptera sp. |
| CMIII (small basic peptide building block from maize grain) | plant pathogens e.g. *Fusarium*, *Alternaria*, *Sclerotina* |
| Com-SAFP (zeamatin) | plant pathogens, e.g. *Fusarium*, *Alternaria*, *Sclerotina*, *Rhizoctonia*, *Chaetomium*, Phycomycen |
| Hm1-gene | *Cochliobulus* |
| chitinases | plant pathogens |
| glucanases | plant pathogens |
| envelope proteins | viruses, such as the Maize dwarf mosaic virus (MDMV) |
| toxins of *Bacillus thuringiensis*, VIP 3, *Bacillus cereus* toxin, *Photorabdus* and *Xenorhabdus* toxins | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., *Aprotis ipsilon*, Asian corn borer, weevils |
| 3-hydroxysteroid oxidase | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., *Aprotis ipsilon*, Asian corn borer, weevils |
| peroxidase | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., *Aprotis ipsilon*, Asian corn borer, weevils |
| aminopeptidase inhibitors, e.g. leucine aminopeptidase inhibitors (LAPI) | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., *Aprotis ipsilon*, Asian corn borer, weevils |

TABLE 1-continued

| | |
|---|---|
| limonene synthase | Western corn rootworm |
| lectin | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., *Aprotis ipsilon*, Asian corn borer, weevils |
| protease inhibitors e.g. cystatin, patatin, virgiferin, CPTI | weevils, Western corn rootworm |
| ribosome-inactivating protein | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., *Aprotis ipsilon*, Asian corn borer, weevils |
| 5C9-maize polypeptide | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., *Aprotis ipsilon*, Asian corn borer, weevils |
| HMG-CoA reductase | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., *Aprotis ipsilon*, Asian corn borer, weevils |

Plant: Wheat

| Structure affected/protein expressed | Feature of the plant/tolerance to |
|---|---|
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acid, cyclohexanedione |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 | xenobiotics and herbicides, such as sulphonylurea compounds |
| antifungal polypeptide AlyAFP | plant pathogens, e.g. *Septoria* and *Fusarium* |
| glucose oxidase | plant pathogens, e.g. *Fusarium*, *Septoria* |
| pyrrolnitrin synthesis gene | plant pathogens, e.g. *Fusarium*, *Septoria* |
| serine/threonine kinases | plant pathogens, e.g. *Fusarium*, *Septoria* and other diseases |
| polypeptide having the effect of triggering a hypersensitivity reaction | plant pathogens, e.g. *Fusarium*, *Septoria* and other diseases |
| systemic aquired resistance (SAR) genes | viral, bacterial, fungal and nematodal pathogens |
| chitinases | plant pathogens |
| glucanases | plant pathogens |
| double-strand ribonuclease | viruses such as, for example, BYDV and MSMV |
| envelope proteins | viruses such as, for example, BYDV and MSMV |
| toxins of *Bacillus thuringiensis*, VIP 3, *Bacillus cereus* toxins, *Photorabdus* and *Xenorhabdus* toxins | Lepidoptera, Coleoptera, Diptera, nematodes |
| 3-hydroxysteroid oxidase | Lepidoptera, Coleoptera, Diptera, nematodes |
| peroxidase | Lepidoptera, Coleoptera, Diptera, nematodes |
| aminopeptidase inhibitors, e.g. leucine aminopeptidase inhibitor | Lepidoptera, Coleoptera, Diptera, nematodes |
| lectins | Lepidoptera, Coleoptera, Diptera, nematodes, aphids |

TABLE 1-continued

| | |
|---|---|
| protease inhibitors, e.g. cystatin, patatin, virgiferin, CPTI | Lepidoptera, Coleoptera, Diptera, nematodes, aphids |
| ribosome-inactivating protein | Lepidoptera, Coleoptera, Diptera, nematodes, aphids |
| HMG-CoA reductase | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., *Aprotis ipsilon*, Asian corn borer, weevils |

Plant: Barley

| Structure affected/protein expressed | Feature of the plant/tolerance to |
|---|---|
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 | xenobiotics and herbicides, such as sulphonylurea compounds |
| antifungal polypeptide AlyAFP | plant pathogens, e.g. *Septoria* and *Fusarium* |
| glucose oxidase | plant pathogens, e.g. *Fusarium*, *Septoria* |
| pyrrolnitrin synthesis gene | plant pathogens, e.g. *Fusarium*, *Septoria* |
| serine/threonine kinases | plant pathogens, e.g. *Fusarium*, *Septoria* and other diseases |
| polypeptide having the effect of triggering a hypersensitivity reaction | plant pathogens, e.g. *Fusarium*, *Septoria* and other diseases |
| systemic aquired resistance (SAR) genes | viral, bacterial, fungal and nematodal pathogens |
| chitinases | plant pathogens |
| glucanases | plant pathogens |
| double-strand ribonuclease | viruses such as, for example, BYDV and MSMV |
| envelope proteins | viruses such as, for example, BYDV and MSMV |
| toxins of *Bacillus thuringiensis*, VIP 3, *Bacillus cereus* toxins, *Photorabdus* and *Xenorhabdus* toxins | Lepidoptera, Coleoptera, Diptera, nematodes |
| 3-hydroxysteroid oxidase | Lepidoptera, Coleoptera, Diptera, nematodes |
| peroxidase | Lepidoptera, Coleoptera, Diptera, nematodes |
| aminopeptidase inhibitors, e.g. leucine aminopeptidase inhibitor | Lepidoptera, Coleoptera, Diptera, nematodes |
| lectins | Lepidoptera, Coleoptera, Diptera, nematodes, aphids |
| protease inhibitors, e.g. cystatin, patatin, virgiferin, CPTI | Lepidoptera, Coleoptera, Diptera, nematodes, aphids |
| ribosome-inactivating protein | Lepidoptera, Coleoptera, Diptera, nematodes, aphids |
| HMG-CoA reductase | Lepidoptera, Coleoptera, Diptera, nematodes, aphids |

Plant: Rice

| Structure affected/principle expressed | Feature of the plant/tolerance to |
|---|---|
| acetolactate synthase (ALS) | sulphonylurea compounds, imidazolinones triazolepyrimidines, pyrimidyloxybenzoates, phthalides |

TABLE 1-continued

| | |
|---|---|
| acetyl-CoA carboxylase (ACCase) | aryloxyphenoxyalkanecarboxylic acid, cyclohexanedione |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 | xenobiotics and herbicides, such as sulphonylurea compounds |
| antifungal polypeptide AlyAFP | plant pathogens |
| glucose oxidase | plant pathogens |
| pyrrolnitrin synthesis gene | plant pathogens |
| serine/threonine kinases | plant pathogens |
| phenylalanine ammonia lyase (PAL) | plant pathogens, e.g. bacterial foliar mildew and inducible rice blast |
| phytoalexins | plant pathogens, e.g. bacterial foliar mildew and rice blast |
| B-1,3-glucanase (antisense) | plant pathogens, e.g. bacterial foliar mildew and rice blast |
| receptor kinase | plant pathogens, e.g. bacterial foliar mildew and rice blast |
| polypeptide having the effect of triggering a hypersensitivity reaction | plant pathogens |
| systemic aquired resistance (SAR) genes | viral, bacterial, fungal and nematodal pathogens |
| chitinases | plant pathogens, e.g. bacterial foliar mildew and rice blast |
| glucanases | plant pathogens |
| double-strand ribonuclease | viruses such as, for example, BYDV and MSMV |
| envelope proteins | viruses such as, for example, BYDV and MSMV |
| toxins of *Bacillus thuringiensis*, VIP 3, *Bacillus cereus* toxins, *Photorabdus* and *Xenorhabdus* toxins | Lepidoptera, e.g. stem borer, Coleoptera, e.g. weevils such as *Lissorhoptrus oryzophilus*, Diptera, rice planthoppers, e.g. rice brown planthopper |
| 3-hydroxysteroid oxidase | Lepidoptera, e.g. stem borer, Coleoptera, e.g. weevils such *as Lissorhoptrus oryzophilus*, Diptera, rice planthoppers, e.g. rice brown planthopper |
| peroxidase | Lepidoptera, e.g. stem borer, Coleoptera, e.g. weevils such as *Lissorhoptrus oryzophilus*, Diptera, rice planthoppers, e.g. rice brown planthopper |
| aminopeptidase inhibitors, e.g. leucine aminopeptidase inhibitor | Lepidoptera, e.g. stem borer, Coleoptera, e.g. weevils such as *Lissorhoptrus oryzophilus*, Diptera, rice planthoppers, e.g. rice brown planthopper |
| lectins | Lepidoptera, e.g. stem borer, Coleoptera, e.g. weevils such as *Lissorhoptrus oryzophilus*, Diptera, rice planthoppers, e.g. rice brown planthopper |
| protease inhibitors | Lepidoptera, e.g. stem borer, Coleoptera, e.g. weevils such as *Lissorhoptrus oryzophilus*, Diptera, rice planthoppers e.g. rice brown planthopper |
| ribosome-inactivating protein | Lepidoptera, e.g. stem borer, Coleoptera, e.g. weevils such as *Lissorhoptrus oryzophilus*, Diptera, rice planthoppers, e.g. rice brown planthopper |
| HMG-CoA reductase | Lepidoptera, e.g. stem borer, Coleoptera, e.g. weevils such as *Lissorhoptrus oryzophilus*, Diptera, rice planthoppers e.g. rice brown planthopper |

TABLE 1-continued

| Plant: Soya bean | |
|---|---|
| Structure affected/principle expressed | Feature of the plant/tolerance to |
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides, such as sulphonylurea compounds |
| antifungal polypeptide AlyAFP | bacterial and fungal pathogens such as, for example, *Fusarium*, *Sclerotinia*, stem rot |
| oxalate oxidase | bacterial and fungal pathogens such as, for example, *Fusarium*, *Sclerotinia*, stem rot |
| glucose oxidase | bacterial and fungal pathogens such as, for example, *Fusarium*, *Sclerotinia*, stem rot |
| pyrrolnitrin synthesis gene | bacterial and fungal pathogens such as, for example, *Fusarium*, *Sclerotinia*, stem rot |
| serine/threonine kinases | bacterial and fungal pathogens such as, for example, *Fusarium*, *Sclerotinia*, stem rot |
| phenylalanine ammonia lyase (PAL) | bacterial and fungal pathogens such as, for example, *Fusarium*, *Sclerotinia*, stem rot |
| phytoalexins | plant pathogens, e.g. bacterial foliar mildew and rice blast |
| B-1,3-glucanase (antisense) | plant pathogens, e.g. bacterial foliar mildew and rice blast |
| receptor kinase | bacterial and fungal pathogens such as, for example, *Fusarium*, *Sclerotinia*, stem rot |
| polypeptide having the effect of triggering a hypersensitivity reaction | plant pathogens |
| systemic aquired resistance (SAR) genes | viral, bacterial, fungal and nematodal pathogens |
| chitinases | bacterial and fungal pathogens such as, for example, *Fusarium*, *Sclerotinia*, stem rot |
| glucanases | bacterial and fungal pathogens such as, for example, *Fusarium*, *Sclerotinia*, stem rot |
| double-strand ribonuclease | viruses such as, for example, BPMV and SbMV |
| envelope proteins | viruses such as, for example, BYDV and MSMV |
| toxins of *Bacillus thuringiensis*, VIP 3, *Bacillus cereus* toxins, *Photorabdus* and *Xenorhabdus* toxins | Lepidoptera, Coleoptera, aphids |
| 3-hydroxysteroid oxidase | Lepidoptera, Coleoptera, aphids |
| peroxidase | Lepidoptera, Coleoptera, aphids |
| aminopeptidase inhibitors, e.g. leucine aminopeptidase inhibitor | Lepidoptera, Coleoptera, aphids |
| lectins | Lepidoptera, Coleoptera, aphids |
| protease inhibitors, e.g. virgiferin | Lepidoptera, Coleoptera, aphids |
| ribosome-inactivating protein | Lepidoptera, Coleoptera, aphids |
| HMG-CoA reductase | Lepidoptera, Coleoptera, aphids |
| barnase | nematodes, e.g. root-knot nematodes and cyst nematodes |
| hatching factor for cyst nematodes | cyst nematodes |
| principles for preventing food uptake | nematodes, e.g. root-knot nematodes and cyst nematodes |

TABLE 1-continued

| Plant: Potato | |
|---|---|
| Structure affected/protein expressed | Feature of the plant/tolerance to |
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides, such as sulphonylurea compounds |
| polyphenol oxidase or polyphenol oxidase (antisense) | black spot |
| metallothionein | bacterial and fungal pathogens such as, for example, *Phytophtora*, |
| ribonuclease | *Phytophtora*, *Verticillium*, *Rhizoctonia* |
| antifungal polypeptide AlyAFP | bacterial and fungal pathogens such as, for example, *Phytophtora* |
| oxalate oxidase | bacterial and fungal pathogens such as, for example, *Phytophtora*, *Verticillium*, *Rhizoctonia* |
| glucose oxidase | bacterial and fungal pathogens such as, for example, *Phytophtora*, *Verticillium*, *Rhizoctonia* |
| pyrrolnitrin synthesis gene | bacterial and fungal pathogens such as, for example, *Phytophtora*, *Verticillium*, *Rhizoctonia* |
| serine/threonine kinases | bacterial and fungal pathogens such as, for example, *Phytophtora*, *Verticillium*, *Rhizoctonia* |
| cecropin B | bacteria such as, for example, *Corynebacterium sepedonicum*, *Erwinia carotovora* |
| phenylalanine ammonia lyase (PAL) | bacterial and fungal pathogens such as, for example, *Phytophtora*, *Verticillium*, *Rhizoctonia* |
| phytoalexins | bacterial and fungal pathogens such as, for example, *Phytophtora*, *Verticillium*, *Rhizoctonia* |
| B-1,3-glucanase (antisense) | bacterial and fungal pathogens such as, for example, *Phytophtora*, *Verticillium*, *Rhizoctonia* |
| receptor kinase | bacterial and fungal pathogens such as, for example, *Phytophtora*, *Verticillium*, *Rhizoctonia* |
| polypeptide having the effect of triggering a hypersensitivity reaction | bacterial and fungal pathogens such as, for example, *Phytophtora*, *Verticillium*, *Rhizoctonia* |
| systemic aquired resistance (SAR) genes | viral, bacterial, fungal and nematodal pathogens |
| chitinases | bacterial and fungal pathogens such as, for example, *Phytophtora*, *Verticillium*, *Rhizoctonia* |
| barnase | bacterial and fungal pathogens such as, for example, *Phytophtora*, *Verticillium*, *Rhizoctonia* |
| gene 49 for controlling disease resistance | bacterial and fungal pathogens such as, for example, *Phytophtora*, *Verticillium*, *Rhizoctonia* |
| trans-aldolase (antisense) | black spot |
| glucanases | bacterial and fungal pathogens such as, for example, *Phytophtora*, *Verticillium*, *Rhizoctonia* |
| double-strand ribonuclease | viruses such as, for example, PLRV, PVY and TRV |
| envelope proteins | viruses such as, for example, PLRV, PVY and TRV |
| 17 kDa or 60 kDa protein | viruses such as, for example, PLRV, PVY and TRV |
| nuclear inclusion proteins, e.g. a or b | viruses such as, for example, PLRV, PVY and TRV |
| pseudoubiquitin | viruses such as, for example, PLRV, PVY and TRV |
| replicase | viruses such as, for example, PLRV, PVY and TRV |

TABLE 1-continued

| | |
|---|---|
| toxins of *Bacillus thuringiensis*, VIP 3, *Bacillus cereus* toxins, *Photorabdus* and *Xenorhabdus* toxins | Coleoptera, e.g. Colorado beetle, aphids |
| 3-hydroxysteroid oxidase | Coleoptera, e.g. Colorado beetle, aphids |
| peroxidase | Coleoptera, e.g. Colorado beetle, aphids |
| aminopeptidase inhibitors, e.g. leucine aminopeptidase inhibitor | Coleoptera, e.g. Colorado beetle, aphids |
| stilbene synthase | Coleoptera, e.g. Colorado beetle, aphids |
| lectins | Coleoptera, e.g. Colorado beetle, aphids |
| protease inhibitors, e.g. cystatin, patatin | Coleoptera, e.g. Colorado beetle, aphids |
| ribosomene-inactivating protein | Coleoptera, e.g. Colorado beetle, aphids |
| HMG-CoA reductase | Coleoptera, e.g. Colorado beetle, aphids |
| hatching factor for cyst nematodes | cyst nematodes |
| barnase | nematodes, e.g. root-knot nematodes and cyst nematodes |
| principles for preventing food uptake | nematodes, e.g. root-knot nematodes and cyst nematodes |

Plant: Tomato

| Structure affected/principle expressed | Feature of the plant/tolerance to |
|---|---|
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acid, cyclohexanedione |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| Cytochrome P450 e.g. P450 SU1 or selection | xenobiotics and herbicides, such as sulphonylurea compounds |
| polyphenol oxidase or polyphenol oxidase (antisense) | black spot |
| metallothionein | bacterial and fungal pathogens such as, for example, *Phytophtora* |
| ribonuclease | *Phytophtora*, *Verticillium*, *Rhizoctonia* |
| antifungal polypeptide AlyAFP | bacterial and fungal pathogens such as, for example, bacterial blotch, *Fusarium*, soft rot, powdery mildew, foliar blight, leaf mould etc. |
| oxalate oxidase | bacterial and fungal pathogens such as, for example, bacterial blotch, *Fusarium*, soft rot, powdery mildew, foliar blight, leaf mould etc. |
| glucose oxidase | bacterial and fungal pathogens such as, for example, bacterial blotch, *Fusarium*, soft rot, powdery mildew, foliar blight, leaf mould etc. |
| pyrrolnitrin synthesis gene | bacterial and fungal pathogens such as, for example, bacterial blotch, *Fusarium*, soft rot, powdery mildew, foliar blight, leaf mould etc. |
| serine/threonine kinases | bacterial and fungal pathogens such as, for example, bacterial blotch, *Fusarium*, soft rot, powdery mildew, foliar blight, leaf mould etc. |
| cecropin B | bacterial and fungal pathogens such as, for example, bacterial blotch, *Fusarium*, soft rot, powdery mildew, foliar blight, leaf mould etc. |
| phenylalanine ammonia lyase (PAL) | bacterial and fungal pathogens such as, for example, bacterial blotch, *Fusarium*, soft rot, powdery mildew, foliar blight, leaf mould etc. |

TABLE 1-continued

| | |
|---|---|
| Cf genes, e.g. Cf 9 Cf5 Cf4 Cf2 | leaf mould |
| osmotin | early blight |
| alpha hordothionin | bakteria |
| systemin | bacterial and fungal pathogens such as, for example, bacterial blotch, *Fusarium*, soft rot, powdery mildew, foliar blight, leaf mould etc. |
| polygalacturonase inhibitors | bacterial and fungal pathogens such as, for example, bacterial blotch, *Fusarium*, soft rot, powdery mildew, foliar blight, leaf mould etc. |
| Prf control gene | bacterial and fungal pathogens such as, for example, bacterial blotch, *Fusarium*, soft rot, powdery mildew, foliar blight, leaf mould etc. |
| 12 *fusarium* resistance site | *Fusarium* |
| phytoalexins | bacterial and fungal pathogens such as, for example, bacterial blotch, *Fusarium*, soft rot, powdery mildew, foliar blight, leaf mould etc. |
| B-1,3-glucanase (antisense) | bacterial and fungal pathogens such as, for example, bacterial blotch, *Fusarium*, soft rot, powdery mildew, foliar blight, leaf mould etc. |
| receptor kinase | bacterial and fungal pathogens such as, for example, bacterial blotch, *Fusarium*, soft rot, powdery mildew, foliar blight, leaf mould etc. |
| polypeptide having the effect of triggering a hypersensitivity reaction | bacterial and fungal pathogens such as, for example, bacterial blotch, *Fusarium*, soft rot, powdery mildew, foliar blight, leaf mould etc. |
| systemic aquired resistance (SAR) genes | viral, bacterial, fungal and nematodal pathogens |
| chitinases | bacterial and fungal pathogens such as, for example, bacterial blotch, *Fusarium*, soft rot, powdery mildew, foliar blight, leaf mould etc. |
| barnase | bacterial and fungal pathogens such as, for example, bacterial blotch, *Fusarium*, soft rot, powdery mildew, foliar blight, leaf mould etc. |
| glucanases | bacterial and fungal pathogens such as, for example, bacterial blotch, *Fusarium*, soft rot, powdery mildew, foliar blight, leaf mould etc. |
| double-strand ribonuclease | viruses such as, for example, PLRV, PVY and ToMoV |
| envelope proteins | viruses such as, for example, PLRV, PVY and ToMoV |
| 17 kDa or 60 kDa protein | viruses such as, for example, PLRV, PVY and ToMoV |
| nuclear inclusion proteins e.g. a or b or | viruses such as, for example, PLRV, PVY and ToMoV |
| nucleoprotein | TRV |
| pseudoubiquitin | viruses such as, for example, PLRV, PVY and ToMoV |
| replicase | viruses such as, for example, PLRV, PVY and ToMoV |
| toxins of *Bacillus thuringiensis*, VIP 3, *Bacillus cereus* toxins, *Photorabdus* and *Xenorhabdus* toxins | Lepidoptera e.g. *Heliothis*, whitefly aphids |
| 3-hydroxysteroid oxidase | Lepidoptera e.g. *Heliothis*, whitefly, aphids |
| peroxidase | Lepidoptera e.g. *Heliothis*, whitefly, aphids |
| aminopeptidase inhibitors, e.g. leucine aminopeptidase inhibitor | Lepidoptera e.g. *Heliothis*, whitefly, aphids |
| lectins | Lepidoptera e.g. *Heliothis*, whitefly, aphids |
| protease inhibitors, e.g. cystatin, patatin | Lepidoptera e.g. *Heliothis*, whitefly, aphids |
| ribosome-inactivating protein | Lepidoptera e.g. *Heliothis*, whitefly, aphids |
| stilbene synthase | Lepidoptera e.g. *Heliothis*, whitefly, aphids |
| HMG-CoA reductase | Lepidoptera e.g. *Heliothis*, whitefly, aphids |

TABLE 1-continued

| | |
|---|---|
| hatching factor for cyst nematodes | cyst nematodes |
| barnase | nematodes, e.g. root-knot nematodes and cyst nematodes |
| principles for preventing food uptake | nematodes, e.g. root-knot nematodes and cyst nematodes |

Plant: Bell Pepper

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial and fungal pathogens |
| metallothionein | bacterial and fungal pathogens |
| ribonuclease | bacterial and fungal pathogens |
| antifungal polypeptid AlyAFP | bacterial and fungal pathogens |
| oxalate oxidase | bacterial and fungal pathogens |
| glucose oxidase | bacterial and fungal pathogens |
| pyrrolnitrin synthesis genes | bacterial and fungal pathogens |
| serine/threonine kinases | bacterial and fungal pathogens |
| cecropin B | bacterial and fungal pathogens, rot, leaf mould, etc. |
| phenylalanine ammonia lyase (PAL) | bacterial and fungal pathogens |
| Cf genes, e.g. Cf9 Ct5 Cf4 Cf2 | bacterial and fungal pathogens |
| osmotin | bacterial and fungal pathogens |
| alpha hordothionine | bacterial and fungal pathogens |
| systemin | bacterial and fungal pathogens |
| polygalacturonase inhibitors | bacterial and fungal pathogens |
| Prf control gene | bacterial and fungal pathogens |
| 12 *Fusarium* resistance site | *Fusarium* |
| phytoalexins | bacterial and fungal pathogens |
| B-1,3-glucanase (antisense) | bacterial and fungal pathogens |
| receptor kinase | bacterial and fungal pathogens |
| polypeptide having the effect of triggering a hypersensitivity reaction | bacterial and fungal pathogens |
| systemic aquired resistance (SAR) genes | viral, bacterial, fungal and nematodal pathogens |
| chitinases | bacterial and fungal pathogens |
| barnase | bacterial and fungal pathogens |
| glucanases | bacterial and fungal pathogens |
| double-strand ribonuclease | viruses such as, for example, CMV, TEV |
| envelope proteins | viruses such as, for example, CMV, TEV |
| 17 kDa or 60 kDa protein | viruses such as, for example, CMV, TEV |
| nuclear inclusion proteins e.g. a or b or nucleoprotein | viruses such as, for example, CMV, TEV |
| pseudoubiquitin | viruses such as, for example, CMV, TEV |
| replicase | viruses such as, for example, CMV, TEV |
| toxins of *Bacillus thuringiensis*, VIP 3, *Bacillus cereus* toxins, *Photorabdus* and *Xenorhabdus* toxins | Lepidoptera, whitefly, aphids |
| 3-hydroxysteroid oxidase | Lepidoptera, whitefly, aphids |
| peroxidase | Lepidoptera, whitefly, aphids |
| aminopeptidase inhibitors, e.g. leucine aminopeptidase inhibitor | Lepidoptera, whitefly, aphids |
| lectins | Lepidoptera, whitefly, aphids |
| protease inhibitors, e.g. cystatin, patatin | Lepidoptera, whitefly, aphids |

TABLE 1-continued

| | |
|---|---|
| ribosome-inactivating protein | Lepidoptera, whitefly, aphids |
| stilbene synthase | Lepidoptera, whitefly, aphids |
| HMG-CoA reductase | Lepidoptera, whitefly, aphids |
| hatching factor for cyst nematodes | cyst nematodes |
| barnase | nematodes, e.g. root-knot nematodes and cyst nematodes |
| principles for preventing food uptake | nematodes, e.g. root-knot nematodes and cyst nematodes |

Plant: Grapevines

| Structure affected/principle expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial and fungal pathogens such as *Botrytis* and powdery mildew |
| metallothionein | bacterial and fungal pathogens such as *Botrytis* and powdery mildew |
| ribonuclease | bacterial and fungal pathogens such as *Botrytis* and powdery mildew |
| antifungal polypeptide AlyAFP | bacterial and fungal pathogens such as *Botrytis* and powdery mildew |
| oxalate oxidase | bacterial and fungal pathogens such as *Botrytis* and powdery mildew |
| glucose oxidase | bacterial and fungal pathogens such as *Botrytis* and powdery mildew |
| pyrrolnitrin synthesis genes | bacterial and fungal pathogens such as *Botrytis* and powdery mildew |
| serine/threonine kinases | bacterial and fungal pathogens such as *Botrytis* and powdery mildew |
| cecropin B | bacterial and fungal pathogens such as *Botrytis* and powdery mildew |
| phenylalanine ammonia lyase (PAL) | bacterial and fungal pathogens such as *Botrytis* and powdery mildew |
| Cf genes, e.g. Cf9 Cf5 Cf4 Cf2 | bacterial and fungal pathogens such as *Botrytis* and powdery mildew |
| osmotin | bacterial and fungal pathogens such as *Botrytis* and powdery mildew |
| alpha hordothionine | bacterial and fungal pathogens such as *Botrytis* and powdery mildew |
| systemin | bacterial and fungal pathogens such as *Botrytis* and powdery mildew |
| polygalacturonase inhibitors | bacterial and fungal pathogens such as *Botrytis* and powdery mildew |
| Prf control gene | bacterial and fungal pathogens such as *Botrytis* and powdery mildew |
| phytoalexins | bacterial and fungal pathogens such as *Botrytis* and powdery mildew |
| B-1,3-glucanase (antisense) | bacterial and fungal pathogens such as *Botrytis* and powdery mildew |
| receptor kinase | bacterial and fungal pathogens such as *Botrytis* and powdery mildew |
| polypeptide having the effect of triggering a hypersensitivity reaction | bacterial and fungal pathogens such as *Botrytis* and powdery mildew |
| systemic aquired resistance (SAR) genes | viral, bacterial, fungal and nematodal pathogens |

TABLE 1-continued

| | |
|---|---|
| chitinases | bacterial and fungal pathogens such as *Botrytis* and powdery mildew |
| barnase | bacterial and fungal pathogens such as *Botrytis* and powdery mildew |
| glucanases | bacterial and fungal pathogens such as *Botrytis* and powdery mildew |
| double-strand ribonuclease | viruses |
| envelope proteins | viruses |
| 17 kDa or 60 kDa protein | viruses |
| nuclear inclusion proteins e.g. a or b or nucleoprotein | viruses |
| pseudoubiquitin | viruses |
| replicase | viruses |
| toxins of *Bacillus thuringiensis*, VIP 3, *Bacillus cereus* toxins, *Photorabdus* and *Xenorhabdus* toxins | Lepidoptera, aphids |
| 3-hydroxysteroid oxidase | Lepidoptera, aphids |
| peroxidase | Lepidoptera, aphids |
| aminopeptidase inhibitors, e.g. leucine aminopeptidase inhibitor | Lepidoptera, aphids |
| lectins | Lepidoptera, aphids |
| protease inhibitors, e.g. cystatin, patatin | Lepidoptera, aphids |
| ribosome-inactivating protein | Lepidoptera, aphids |
| stilbene synthase | Lepidoptera, aphids, diseases |
| HMG-CoA reductase | Lepidoptera, aphids |
| hatching factor for cyst nematodes | cyst nematodes |
| barnase | nematodes, e.g. root-knot nematodes and cyst nematodes or general diseases |
| CBI | root-knot nematodes |
| principles for preventing food uptake | nematodes, e.g. root-knot nematodes or root-cyst nematodes |

Plant: Oilseed rape

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial and fungal pathogens such as *Cylindrosporium*, *Phoma*, *Sclerotinia* |
| metallothionein | bacterial and fungal pathogens such as *Cylindrosporium*, *Phoma*, *Sclerotinia* |
| ribonuclease | bacterial and fungal pathogens such as *Cylindrosporium*, *Phoma*, *Sclerotinia* |
| antifungal polypeptid AlyAFP | bacterial and fungal pathogens such as *Cylindrosporium*, *Phoma*, *Sclerotinia* |
| oxalate oxidase | bacterial and fungal pathogens such as *Cylindrosporium*, *Phoma*, *Sclerotinia* |
| glucose oxidase | bacterial and fungal pathogens such as *Cylindrosporium*, *Phoma*, *Sclerotinia* |
| pyrrolnitrin synthesis genes | bacterial and fungal pathogens such as *Cylindrosporium*, *Phoma*, *Sclerotinia* |
| serine/threonine kinases | bacterial and fungal pathogens such as *Cylindrosporium*, *Phoma*, *Sclerotinia* |
| cecropin B | bacterial and fungal pathogens such as *Cylindrosporium*, *Phoma*, *Sclerotinia* |

TABLE 1-continued

| | |
|---|---|
| phenylalanine ammonia lyase (PAL) | bacterial and fungal pathogens such as *Cylindrosporium*, *Phoma*, *Sclerotinia* |
| Cf genes, e.g. Cf 9 Cf5 Cf4 Cf2 | bacterial and fungal pathogens such as *Cylindrosporium*, *Phoma*, *Sclerotinia* |
| osmotin | bacterial and fungal pathogens such as *Cylindrosporium*, *Phoma*, *Sclerotinia* |
| alpha hordothionine | bacterial and fungal pathogens such as *Cylindrosporium*, *Phoma*, *Sclerotinia* |
| systemin | bacterial and fungal pathogens such as *Cylindrosporium*, *Phoma*, *Sclerotinia* |
| polygalacturonase inhibitors | bacterial and fungal pathogens such as *Cylindrosporium*, *Phoma*, *Sclerotinia* |
| Prf control gene | bacterial and fungal pathogens such as *Cylindrosporium*, *Phoma*, *Sclerotinia* |
| phytoalexins | bacterial and fungal pathogens such as *Cylindrosporium*, *Phoma*, *Sclerotinia* |
| B-1,3-glucanase (antisense) | bacterial and fungal pathogens such as *Cylindrosporium*, *Phoma*, *Sclerotinia* |
| receptor kinase | bacterial and fungal pathogens such as *Cylindrosporium*, *Phoma*, *Sclerotinia* |
| polypeptide having the effect of triggering a hypersensitivity reaction | bacterial and fungal pathogens such as *Cylindrosporium*, *Phoma*, *Sclerotinia* |
| systemic aquired resistance (SAR) genes | viral, bacterial, fungal and nematodal pathogens |
| chitinases | bacterial and fungal pathogens such as *Cylindrosporium*, *Phoma*, *Sclerotinia* |
| barnase | bacterial and fungal pathogens such as *Cylindrosporium*, *Phoma*, *Sclerotinia* nematodes |
| glucanases | bacterial and fungal pathogens such as *Cylindrosporium*, *Phoma*, *Sclerotinia* |
| double-strand ribonuclease | viruses |
| envelope proteins | viruses |
| 17 kDa or 60 kDa protein | viruses |
| nuclear inclusion proteins e.g. a or b or nucleoprotein | viruses |
| pseudoubiquitin | viruses |
| replicase | viruses |
| toxins of *Bacillus thuringiensis*, VIP 3, *Bacillus cereus* toxins, *Photorabdus* and *Xenorhabdus* toxins | Lepidoptera, aphids |
| 3-hydroxysteroid oxidase | Lepidoptera, aphids |
| peroxidase | Lepidoptera, aphids |
| aminopeptidase inhibitors, e.g. leucine aminopeptidase inhibitor | Lepidoptera, aphids |
| lectins | Lepidoptera, aphids |
| protease inhibitors, e.g. cystatin, patatin, CPTI | Lepidoptera, aphids |
| ribosome-inactivating protein | Lepidoptera, aphids |
| stilbene synthase | Lepidoptera, aphids, diseases |
| HMG-CoA reductase | Lepidoptera, aphids |
| hatching factor for cyst nematodes | cyst nematodes |
| barnase | nematodes, e.g. root-knot nematodes and cyst nematodes |
| CBI | root-knot nematodes |
| principles for preventing food uptake induced at nematode feeding sites | nematodes, e.g. root-knot nematodes and root-cyst nematodes |

Plant: *Brassica* vegetables (cabbage, Brussels sprouts etc.)

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |

TABLE 1-continued

| | |
|---|---|
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial and fungal pathogens |
| metallothionein | bacterial and fungal pathogens |
| ribonuclease | bacterial and fungal pathogens |
| antifungal polypeptid AlyAFP | bacterial and fungal pathogens |
| oxalate oxidase | bacterial and fungal pathogens |
| glucose oxidase | bacterial and fungal pathogens |
| pyrrolnitrin synthesis genes | bacterial and fungal pathogens |
| serine/threonine kinases | bacterial and fungal pathogens |
| cecropin B | bacterial and fungal pathogens |
| phenylalanine ammonia lyase (PAL) | bacterial and fungal pathogens |
| Cf genes, e.g. Cf 9 Cf5 Cf4 Cf2 | bacterial and fungal pathogens |
| osmotin | bacterial and fungal pathogens |
| alpha hordothionine | bacterial and fungal pathogens |
| systemin | bacterial and fungal pathogens |
| polygalacturonase inhibitors | bacterial and fungal pathogens |
| Prf control gene | bacterial and fungal pathogens |
| phytoalexins | bacterial and fungal pathogens |
| B-1,3-glucanase (antisense) | bacterial and fungal pathogens |
| receptor kinase | bacterial and fungal pathogens |
| polypeptide having the effect of triggering a hypersensitivity reaction | bacterial and fungal pathogens |
| systemic aquired resistance (SAR) genes | viral, bacterial, fungal and nematodal pathogens |
| chitinases | bacterial and fungal pathogens |
| barnase | bacterial and fungal pathogens |
| glucanases | bacterial and fungal pathogens |
| double-strand ribonuclease | viruses |
| envelope proteins | viruses |
| 17 kDa or 60 kDa protein | viruses |
| nuclear inclusion proteins e.g. a or b or nucleoprotein | viruses |
| pseudoubiquitin | viruses |
| replicase | viruses |
| toxins of *Bacillus thuringiensis*, VIP 3, *Bacillus cereus* toxins, *Photorabdus* and *Xenorhabdus* toxins | Lepidoptera, aphids |
| 3-hydroxysteroid oxidase | Lepidoptera, aphids |
| peroxidase | Lepidoptera, aphids |
| aminopeptidase inhibitors, e.g. leucine aminopeptidase inhibitor | Lepidoptera, aphids |
| lectins | Lepidoptera, aphids |
| protease inhibitors, e.g. cystatin, patatin, CPTI | Lepidoptera, aphids |
| ribosome-inactivating protein | Lepidoptera, aphids |
| stilbene synthase | Lepidoptera, aphids, diseases |
| HMG-CoA reductase | Lepidoptera, aphids |
| hatching factor for cyst nematodes | cyst nematodes |
| barnase | nematodes, e.g. root-knot nematodes and cyst nematodes |
| CBI | root-knot nematodes |
| principles for preventing food uptake induced at nematode feeding sites | nematodes, e.g. root-knot nematodes and root-cyst nematodes cyst nematodes |

Plants: *Pomaceous* fruit, e.g. apples, pears

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |

TABLE 1-continued

| | |
|---|---|
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial and fungal pathogens such as storage scab on apples or fire-blight |
| metallothionein | bacterial and fungal pathogens such as storage scab on apples or fire-blight |
| ribonuclease | bacterial and fungal pathogens such as storage scab on apples or fire-blight |
| antifungal polypeptid AlyAFP | bacterial and fungal pathogens such as storage scab on apples or fire-blight |
| oxalate oxidase | bacterial and fungal pathogens such as storage scab on apples or fire-blight |
| glucose oxidase | bacterial and fungal pathogens such as storage scab on apples or fire-blight |
| pyrrolnitrin synthesis genes | bacterial and fungal pathogens such as storage scab on apples or fire-blight |
| serine/threonine kinases | bacterial and fungal pathogens such as storage scab on apples or fire-blight |
| cecropin B | bacterial and fungal pathogens such as storage scab on apples or fire-blight |
| phenylalanine ammonia lyase (PAL) | bacterial and fungal pathogens such as storage scab on apples or fire-blight |
| Cf genes, e.g. Cf9 Cf5 Cf4 Cf2 | bacterial and fungal pathogens such as storage scab on apples or fire-blight |
| osmotin | bacterial and fungal pathogens such as storage scab on apples or fire-blight |
| alpha hordothionine | bacterial and fungal pathogens such as storage scab on apples or fire-blight |
| systemin | bacterial and fungal pathogens such as storage scab on apples or fire-blight |
| polygalacturonase inhibitors | bacterial and fungal pathogens such as storage scab on apples or fire-blight |
| Prf control gene | bacterial and fungal pathogens such as storage scab on apples or fire-blight |
| phytoalexins | bacterial and fungal pathogens such as storage scab on apples or fire-blight |
| B-1,3-glucanase (antisense) | bacterial and fungal pathogens such as storage scab on apples or fire-blight |
| receptor kinase | bacterial and fungal pathogens such as storage scab on apples or fire-blight |
| polypeptide having the effect of triggering a hypersensitivity reaction | bacterial and fungal pathogens such as storage scab on apples or fire-blight |
| systemic aquired resistance (SAR) genes | viral, bacterial, fungal and nematodal pathogens |
| lytic protein | bacterial and fungal pathogens such as storage scab on apples or fire-blight |
| lysozyme | bacterial and fungal pathogens such as storage scab on apples or fire-blight |
| chitinases | bacterial and fungal pathogens such as storage scab on apples or fire-blight |
| barnase | bacterial and fungal pathogens such as storage scab on apples or fire-blight |
| glucanases | bacterial and fungal pathogens such as storage scab on apples or fire-blight |
| double-strand ribonuclease | viruses |
| envelope proteins | viruses |
| 17 kDa or 60 kDa protein | viruses |
| nuclear inclusion proteins e.g. a or b or nucleoprotein | viruses |
| pseudoubiquitin | viruses |
| replicase | viruses |
| toxins of *Bacillus thuringiensis*, VIP 3, *Bacillus cereus* toxins, *Photorabdus* and *Xenorhabdus* toxins | Lepidoptera, aphids, mites |
| 3-hydroxysteroid oxidase | Lepidoptera, aphids, mites |
| peroxidase | Lepidoptera, aphids, mites |
| aminopeptidase inhibitors, e.g. leucine aminopeptidase inhibitor | Lepidoptera, aphids, mites |

TABLE 1-continued

| | |
|---|---|
| lectins | Lepidoptera, aphids, mites |
| protease inhibitors, e.g. cystatin, patatin, CPTI | Lepidoptera, aphids, mites |
| ribosome-inactivating protein | Lepidoptera, aphids, mites |
| stilbene synthase | Lepidoptera, aphids, diseases, mites |
| HMG-CoA reductase | Lepidoptera, aphids, mites |
| hatching factor for cyst nematodes | cyst nematodes |
| barnase | nematodes, e.g. root-knot nematodes and cyst nematodes |
| CBI | root-knot nematodes |
| principles for preventing food uptake induced at nematode feeding sites | nematodes, e.g. root-knot nematodes and root-cyst nematodes |

Plant: Melon

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens such as *Phytophtora* |
| metallothionein | bacterial or fungal pathogens such as *Phytophtora* |
| ribonuclease | bacterial or fungal pathogens such as *Phytophtora* |
| antifungal polypeptid AlyAFP | bacterial or fungal pathogens such as *Phytophtora* |
| oxalate oxidase | bacterial or fungal pathogens such as *Phytophtora* |
| glucose oxidase | bacterial or fungal pathogens such as *Phytophtora* |
| pyrrolnitrin synthesis genes | bacterial or fungal pathogens such as *Phytophtora* |
| serine/threonine kinases | bacterial or fungal pathogens such as *Phytophtora* |
| cecropin B | bacterial or fungal pathogens such as *Phytophtora* |
| phenylalanine ammonia lyase (PAL) | bacterial or fungal pathogens such as *Phytophtora* |
| Cf genes, e.g. Cf9 Cf5 Cf4 Cf2 | bacterial or fungal pathogens such as *Phytophtora* |
| osmotin | bacterial or fungal pathogens such as *Phytophtora* |
| alpha hordothionine | bacterial or fungal pathogens such as *Phytophtora* |
| systemin | bacterial or fungal pathogens such as *Phytophtora* |
| polygalacturonase inhibitors | bacterial or fungal pathogens such as *Phytophtora* |
| Prf control gene | bacterial or fungal pathogens such as *Phytophtora* |
| phytoalexins | bacterial or fungal pathogens such as *Phytophtora* |
| B-1,3-glucanase (antisense) | bacterial or fungal pathogens such as *Phytophtora* |
| receptor kinase | bacterial or fungal pathogens such as *Phytophtora* |

TABLE 1-continued

| | |
|---|---|
| polypeptide having the effect of triggering a hypersensitivity reaction | bacterial or fungal pathogens such as *Phytophtora* |
| systemic aquired resistance (SAR) genes | viral, bacterial, fungal and nematodal pathogens |
| lytic protein | bacterial or fungal pathogens such as *Phytophtora* |
| lysozyme | bacterial or fungal pathogens such as *Phytophtora* |
| chitinases | bacterial or fungal pathogens such as *Phytophtora* |
| barnase | bacterial or fungal pathogens such as *Phytophtora* |
| glucanases | bacterial or fungal pathogens such as *Phytophtora* |
| double-strand ribonuclease | viruses such as CMV, PRSV, WMV2, SMV, ZYMV |
| envelope proteins | viruses such as CMV, PRSV, WMV2, SMV, ZYMV |
| 17 kDa or 60 kDa protein | viruses such as CMV, PRSV, WMV2, SMV, ZYMV |
| nuclear inclusion proteins e.g. a or b or nucleoprotein | viruses such as CMV, PRSV, WMV2, SMV, ZYMV |
| pseudoubiquitin | viruses such as CMV, PRSV, WMV2, SMV, ZYMV |
| replicase | viruses such as CMV, PRSV, WMV2, SMV, ZYMV |
| toxins of *Bacillus thuringiensis*, VIP 3, *Bacillus cereus* toxins, *Photorabdus* and *Xenorhabdus* toxins | Lepidoptera, aphids, mites |
| 3-hydroxysteroid oxidase | Lepidoptera, aphids, mites, whitefly |
| peroxidase | Lepidoptera, aphids, mites, whitefly |
| aminopeptidase inhibitors, e.g. leucine aminopeptidase inhibitor | Lepidoptera, aphids, mites, whitefly |
| lectins | Lepidoptera, aphids, mites, whitefly |
| protease inhibitors, e.g. cystatin, patatin, CPTI, virgiferin | Lepidoptera, aphids, mites, whitefly |
| ribosome-inactivating protein | Lepidoptera, aphids, mites, whitefly |
| stilbene synthase | Lepidoptera, aphids, mites, whitefly |
| HMG-CoA reductase | Lepidoptera, aphids, mites, whitefly |
| hatching factor for cyst nematodes | cyst nematodes |
| barnase | nematodes, e.g. root-knot nematodes and cyst nematodes |
| CBI | root-knot nematodes |
| principles for preventing food uptake induced at nematode feeding sites | nematodes, e.g. root-knot nematodes and root-cyst nematodes |

Plant: Banana

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens |
| metallothionein | bacterial or fungal pathogens |
| ribonuclease | bacterial or fungal pathogens |
| antifungal polypeptid AlyAFP | bacterial or fungal pathogens |

TABLE 1-continued

| | |
|---|---|
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| cecropin B | bacterial or fungal pathogens |
| phenylalanine ammonia lyase (PAL) | bacterial or fungal pathogens |
| Cf genes, e.g. Cf9 Cf5 Cf4 Cf2 | bacterial or fungal pathogens |
| osmotin | bacterial or fungal pathogens |
| alpha hordothionine | bacterial or fungal pathogens |
| systemin | bacterial or fungal pathogens |
| polygalacturonase inhibitors | bacterial or fungal pathogens |
| Prf control gene | bacterial or fungal pathogens |
| phytoalexins | bacterial or fungal pathogens |
| B-1,3-glucanase (antisense) | bacterial or fungal pathogens |
| receptor kinase | bacterial or fungal pathogens |
| polypeptide having the effect of triggering a hypersensitivity reaction | bacterial or fungal pathogens |
| systemic aquired resistance (SAR) genes | viral, bacterial, fungal and nematodal pathogens |
| lytic protein | bacterial or fungal pathogens |
| lysozyme | bacterial or fungal pathogens |
| chitinases | bacterial or fungal pathogens |
| barnase | bacterial or fungal pathogens |
| glucanases | bacterial or fungal pathogens |
| double-strand ribonuclease | viruses such as the Banana Bunchy Top Virus (BBTV) |
| envelope proteins | viruses such as the Banana Bunchy Top Virus (BBTV) |
| 17 kDa or 60 kDa protein | viruses such as the Banana Bunchy Top Virus (BBTV) |
| nuclear inclusion proteins e.g. a or b or nucleoprotein | viruses such as the Banana Bunchy Top Virus (BBTV) |
| pseudoubiquitin | viruses such as the Banana Bunchy Top Virus (BBTV) |
| replicase | viruses such as the Banana Bunchy Top Virus (BBTV) |
| toxins of *Bacillus thuringiensis*, VIP 3, *Bacillus cereus* toxins, *Photorabdus* and *Xenorhabdus* toxins | Lepidoptera, aphids, mites, nematodes |
| 3-hydroxysteroid oxidase | Lepidoptera, aphids, mites, nematodes |
| peroxidase | Lepidoptera, aphids, mites, nematodes |
| aminopeptidase inhibitors, e.g. leucine aminopeptidase inhibitor | Lepidoptera, aphids, mites, nematodes |
| lectins | Lepidoptera, aphids, mites, nematodes |
| protease inhibitors, e.g. cystatin, patatin, CPTI, virgiferin | Lepidoptera, aphids, mites, nematodes |
| ribosome-inactivating protein | Lepidoptera, aphids, mites, nematodes |
| stilbene synthase | Lepidoptera, aphids, mites, nematodes |
| HMG-CoA reductase | Lepidoptera, aphids, mites, nematodes |
| hatching factor for cyst nematodes | cyst nematodes |
| barnase | nematodes, e.g. root-knot nematodes and cyst nematodes |
| CBI | root-knot nematodes |
| principles for preventing food uptake induced at nematode feeding sites | nematodes, e.g. root-knot nematodes and root-cyst nematodes |

Plant: Cotton

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthese |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phosphoshikimate synthase (EPSPS) | glyphosate or sulphosate |
| glyphosate oxidoreductase | glyphosate or sulphosate |

TABLE 1-continued

| | |
|---|---|
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens |
| metallothionein | bacterial or fungal pathogens |
| ribonuclease | bacterial or fungal pathogens |
| antifungal polypeptid AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| cecropin B | bacterial or fungal pathogens |
| phenylalanine ammonia lyase (PAL) | bacterial or fungal pathogens |
| Cf genes, e.g. Cf9 Cf5 Cf4 Cf2 | bacterial or fungal pathogens |
| osmotin | bacterial or fungal pathogens |
| alpha hordothionine | bacterial or fungal pathogens |
| systemin | bacterial or fungal pathogens |
| polygalacturonase inhibitors | bacterial or fungal pathogens |
| Prf control gene | bacterial or fungal pathogens |
| phytoalexins | bacterial or fungal pathogens |
| B-1,3-glucanase (antisense) | bacterial or fungal pathogens |
| receptor kinase | bacterial or fungal pathogens |
| polypeptide having the effect of triggering a hypersensitivity reaction | bacterial or fungal pathogens |
| systemic aquired resistance (SAR) genes | viral, bacterial, fungal and nematodal pathogens |
| lytic protein | bacterial or fungal pathogens |
| lysozyme | bacterial or fungal pathogens |
| chitinases | bacterial or fungal pathogens |
| barnase | bacterial or fungal pathogens |
| glucanases | bacterial or fungal pathogens |
| double-strand ribonuclease | viruses such as the wound tumour virus (WTV) |
| envelope proteins | viruses such as the wound tumour virus (WTV) |
| 17 kDa or 60 kDa protein | viruses such as the wound tumour virus (WTV) |
| nuclear inclusion proteins e.g. a or b or nucleoprotein | viruses such as the wound tumour virus (WTV) |
| pseudoubiquitin | viruses such as the wound tumour virus (WTV) |
| replicase | viruses such as the wound tumour virus (WTV) |
| toxins of *Bacillus thuringiensis*, VIP 3, *Bacillus cereus* toxins, *Photorabdus* and *Xenorhabdus* toxins | Lepidoptera, aphids, mites, nematodes, whitefly |
| 3-hydroxysteroid oxidase | Lepidoptera, aphids, mites, nematodes, whitefly |
| peroxidase | Lepidoptera, aphids, mites, nematodes, whitefly |
| aminopeptidase inhibitors, e.g. leucine aminopeptidase inhibitor | Lepidoptera, aphids, mites, nematodes, whitefly |
| lectins | Lepidoptera, aphids, mites, nematodes, whitefly |
| protease inhibitors, e.g. cystatin, patatin, CPTI, virgiferin | Lepidoptera, aphids, mites, nematodes, whitefly |
| ribosome-inactivating protein | Lepidoptera, aphids, mites, nematodes, whitefly |
| stilbene synthase | Lepidoptera, aphids, mites, nematodes, whitefly |
| HMG-CoA reductase | Lepidoptera, aphids, mites, nematodes, whitefly |
| hatching factor for cyst nematodes | cyst nematodes |
| barnase | nematodes, e.g. root-knot nematodes and cyst nematodes |
| CBI | root-knot nematodes |
| principles for preventing food uptake induced at nematode feeding sites | nematodes, e.g. root-knot nematodes and root-cyst nematodes |

Plant: Sugar cane

| Feature affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |

TABLE 1-continued

| | |
|---|---|
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens |
| metallothionein | bacterial or fungal pathogens |
| ribonuclease | bacterial or fungal pathogens |
| antifungal polypeptid AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| cecropin B | bacterial or fungal pathogens |
| phenylalanine ammonia lyase (PAL) | bacterial or fungal pathogens |
| Cf genes, e.g. Cf9 Cf5 Cf4 Cf2 | bacterial or fungal pathogens |
| osmotin | bacterial or fungal pathogens |
| alpha hordothionine | bacterial or fungal pathogens |
| systemin | bacterial or fungal pathogens |
| polygalacturonase inhibitors | bacterial or fungal pathogens |
| Prf control gene | bacterial or fungal pathogens |
| phytoalexins | bacterial or fungal pathogens |
| B-1,3-glucanase (antisense) | bacterial or fungal pathogens |
| receptor kinase | bacterial or fungal pathogens |
| polypeptide having the effect of triggering a hypersensitivity reaction | bacterial or fungal pathogens |
| systemic aquired resistance (SAR) genes | viral, bacterial, fungal and nematodal pathogens |
| lytic protein | bacterial or fungal pathogens |
| lysozyme | bacterial or fungal pathogens, e.g. *Clavibacter* |
| chitinases | bacterial or fungal pathogens |
| barnase | bacterial or fungal pathogens |
| glucanases | bacterial or fungal pathogens |
| double-strand ribonuclease | viruses such as SCMV, SrMV |
| envelope proteins | viruses such as SCMV, SrMV |
| 17 kDa or 60 kDa protein | viruses such as SCMV, SrMV |
| nuclear inclusion proteins e.g. a or b or nucleoprotein | viruses such as SCMV, SrMV |
| pseudoubiquitin | viruses such as SCMV, SrMV |
| replicase | viruses such as SCMV, SrMV |
| toxins of *Bacillus thuringiensis*, VIP 3, *Bacillus cereus* toxins, *Photorabdus* and *Xenorhabdus* toxins | Lepidoptera, aphids, mites, nematodes, whitefly, beetles such as e.g. the Mexican rice borer |
| 3-hydroxysteroid oxidase | Lepidoptera, aphids, mites, nematodes, whitefly, beetles such as e.g. the Mexican rice borer |
| peroxidase | Lepidoptera, aphids, mites, nematodes, whitefly, beetles such as e.g. the Mexican rice borer |
| aminopeptidase inhibitors, e.g. leucine aminopeptidase inhibitor | Lepidoptera, aphids, mites, nematodes, whitefly, beetles such as e.g. the Mexican rice borer |
| lectins | Lepidoptera, aphids, mites, nematodes, whitefly, beetles such as e.g. the Mexican rice borer |
| protease inhibitors, e.g. cystatin, patatin, CPTI, virgiferin | Lepidoptera, aphids, mites, nematodes, whitefly, beetles such as e.g. the Mexican rice borer |
| ribosome-inactivating protein | Lepidoptera, aphids, mites, nematodes, whitefly, beetles such as e.g. the Mexican rice borer |
| stilbene synthase | Lepidoptera, aphids, mites, nematodes, whitefly, beetles such as e.g. the Mexican rice borer |

TABLE 1-continued

| | |
|---|---|
| HMG-CoA reductase | Lepidoptera, aphids, mites, nematodes, whitefly, beetles such as e.g. the Mexican rice borer |
| hatching factor for cyst nematodes | cyst nematodes |
| barnase | nematodes, e.g. root-knot nematodes and cyst nematodes |
| CBI | root-knot nematodes |
| principles for preventing food uptake induced at nematode feeding sites | nematodes, e.g. root-knot nematodes and root-cyst nematodes |

Plant: Sunflower

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens |
| metallothionein | bacterial or fungal pathogens |
| ribonuclease | bacterial or fungal pathogens |
| antifungal polypeptid AlyAFP | bacterial or fungal pathogens |
| oxalate oxidase | bacterial or fungal pathogens, e.g. *Sclerotinia* |
| glucose oxidase | bacterial or fungal pathogens |
| pyrrolnitrin synthesis genes | bacterial or fungal pathogens |
| serine/threonine kinases | bacterial or fungal pathogens |
| cecropin B | bacterial or fungal pathogens |
| phenylalanine ammonia lyase (PAL) | bacterial or fungal pathogens |
| Cf genes, e.g. Cf9 Cf5 Cf4 Cf2 | bacterial or fungal pathogens |
| osmotin | bacterial or fungal pathogens |
| alpha hordothionine | bacterial or fungal pathogens |
| systemin | bacterial or fungal pathogens |
| polygalacturonase inhibitors | bacterial or fungal pathogens |
| Prf control gene | bacterial or fungal pathogens |
| phytoalexins | bacterial or fungal pathogens |
| B-1,3-glucanase (antisense) | bacterial or fungal pathogens |
| receptor kinase | bacterial or fungal pathogens |
| polypeptide having the effect of triggering a hypersensitivity reaction | bacterial or fungal pathogens |
| systemic aquired resistance (SAR) genes | viral, bacterial, fungal and nematodal pathogens |
| lytic protein | bacterial or fungal pathogens |
| lysozyme | bacterial or fungal pathogens |
| chitinases | bacterial or fungal pathogens |
| barnase | bacterial or fungal pathogens |
| glucanases | bacterial or fungal pathogens |
| double-strand ribonuclease | viruses such as CMV, TMV |
| envelope proteins | viruses such as CMV, TMV |
| 17 kDa or 60 kDa protein | viruses such as CMV, TMV |
| nuclear inclusion proteins e.g. a or b or nucleoprotein | viruses such as CMV, TMV |
| pseudoubiquitin | viruses such as CMV, TMV |
| replicase | viruses such as CMV, TMV |
| toxins of *Bacillus thuringiensis*, VIP 3, *Bacillus cereus* toxins, *Photorabdus* and *Xenorhabdus* toxins | Lepidoptera, aphids, mites, nematodes, whitefly, beetles |

TABLE 1-continued

| | |
|---|---|
| 3-hydroxysteroid oxidase | Lepidoptera, aphids, mites, nematodes, whitefly, beetles |
| peroxidase | Lepidoptera, aphids, mites, nematodes, whitefly, beetles |
| aminopeptidase inhibitors, e.g. leucine aminopeptidase inhibitor | Lepidoptera, aphids, mites, nematodes, whitefly, beetles |
| lectins | Lepidoptera, aphids, mites, nematodes, whitefly, beetles |
| protease inhibitors, e.g. cystatin, patatin, CPTI, virgiferin | Lepidoptera, aphids, mites, nematodes, whitefly, beetles |
| ribosome-inactivating protein | Lepidoptera, aphids, mites, nematodes, whitefly, beetles |
| stilbene synthase | Lepidoptera, aphids, mites, nematodes, whitefly, beetles |
| HMG-CoA reductase | Lepidoptera, aphids, mites, nematodes, whitefly, beetles |
| hatching factor for cyst nematodes | cyst nematodes |
| barnase | nematodes, e.g. root-knot nematodes and cyst nematodes |
| CBI | root-knot nematodes |
| principles for preventing food uptake induced at nematode feeding sites | nematodes, e.g. root-knot nematodes and root-cyst nematodes |

Plants: Sugar beet, turnips

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens |
| metallothionein | bacterial or fungal pathogens |
| ribonuclease | bacterial or fungal pathogens |
| antifungal polypeptid AlyAFP | bacterial or fungal pathogens |
| oxalate oxidase | bacterial or fungal pathogens, e.g. *Sclerotinia* |
| glucose oxidase | bacterial or fungal pathogens |
| pyrrolnitrin synthesis genes | bacterial or fungal pathogens |
| serine/threonine kinases | bacterial or fungal pathogens |
| cecropin B | bacterial or fungal pathogens |
| phenylalanine ammonia lyase (PAL) | bacterial or fungal pathogens |
| Cf genes, e.g. Cf 9 Cf5 Cf4 Cf2 | bacterial or fungal pathogens |
| osmotin | bacterial or fungal pathogens |
| alpha hordothionine | bacterial or fungal pathogens |
| systemin | bacterial or fungal pathogens |
| polygalacturonase inhibitors | bacterial or fungal pathogens |
| Prf control gene | bacterial or fungal pathogens |
| phytoalexins | bacterial or fungal pathogens |
| B-1,3-glucanase (antisense) | bacterial or fungal pathogens |
| AX + WIN-proteins | bacterial and fungal pathogens such as *Cercospora beticola* |
| receptor kinase | bacterial or fungal pathogens |
| polypeptide having the effect of triggering a hypersensitivity reaction | bacterial or fungal pathogens |
| systemic aquired resistance (SAR) genes | viral, bacterial, fungal and nematodal pathogens |

TABLE 1-continued

| | |
|---|---|
| lytic protein | bacterial or fungal pathogens |
| lysozyme | bacterial or fungal pathogens |
| chitinases | bacterial or fungal pathogens |
| barnase | bacterial or fungal pathogens |
| glucanases | bacterial or fungal pathogens |
| double-strand ribonuclease | viruses such as, for example, BNYVV |
| envelope proteins | viruses such as, for example, BNYVV |
| 17 kDa or 60 kDa protein | viruses such as, for example, BNYVV |
| nuclear inclusion proteins e.g. a or b or nucleoprotein | viruses such as, for example, BNYVV |
| pseudoubiquitin | viruses such as, for example, BNYVV |
| replicase | viruses such as, for example, BNYVV |
| toxins of *Bacillus thuringiensis*, VIP 3, *Bacillus cereus* toxins, *Photorabdus* and *Xenorhabdus* toxins | Lepidoptera, aphids, mites, nematodes, whitefly, beetles, root-flies |
| 3-hydroxysteroid oxidase | Lepidoptera, aphids, mites, nematodes, whitefly, beetles, root-flies |
| peroxidase | Lepidoptera, aphids, mites, nematodes, whitefly, beetles, root-flies |
| aminopeptidase inhibitors, e.g. leucine aminopeptidase inhibitor | Lepidoptera, aphids, mites, nematodes, whitefly, beetles, root-flies |
| lectins | Lepidoptera, aphids, mites, nematodes, whitefly, beetles, root-flies |
| protease inhibitors, e.g. cystatin, patatin, CPTI, virgiferin | Lepidoptera, aphids, mites, nematodes, whitefly, beetles, root-flies |
| ribosome-inactivating protein | Lepidoptera, aphids, mites, nematodes, whitefly, beetles, root-flies |
| stilbene synthase | Lepidoptera, aphids, mites, nematodes, whitefly, beetles, root-flies |
| HMG-CoA reductase | Lepidoptera, aphids, mites, nematodes, whitefly, beetles, root-flies |
| hatching factor for cyst nematodes | cyst nematodes |
| barnase | nematodes, e.g. root-knot nematodes and cyst nematodes |
| beet cyst nematode resistance site | cyst nematodes |
| CBI | root-knot nematodes |
| principles for preventing food uptake induced | nematodes, e.g. root-knot nematodes and root-cyst nematodes |

TABLE 2

| AP | Control of |
|---|---|
| CrylA(a) | *Adoxophyes* spp. |
| CrylA(a) | *Agrotis* spp. |
| CrylA(a) | *Alabama argiliaceae* |
| CrylA(a) | *Anticarsia gemmatalis* |
| CrylA(a) | *Chilo* spp. |
| CrylA(a) | *Clysia ambiguella* |
| CrylA(a) | *Crocidolomia binotalis* |
| CrylA(a) | *Cydia* spp. |
| CrylA(a) | *Diparopsis castanea* |
| CrylA(a) | *Earias* spp. |
| CrylA(a) | *Ephestia* spp. |
| CrylA(a) | *Heliothis* spp. |
| CrylA(a) | *Heliula undalis* |
| CrylA(a) | *Keiferia lycopersicella* |
| CrylA(a) | *Leucoptera scitella* |
| CrylA(a) | *Lithocollethis* spp. |
| CrylA(a) | *Lobesia botrana* |
| CrylA(a) | *Ostrinia nubilalis* |
| CrylA(a) | *Pandemis* spp. |
| CrylA(a) | *Pectinophora gossyp.* |
| CrylA(a) | *Phyllocnistis citrella* |
| CrylA(a) | *Pieris* spp. |
| CrylA(a) | *Plutella xylostella* |
| CrylA(a) | *Scirpophaga* spp. |
| CrylA(a) | *Sesamia* spp. |
| CrylA(a) | *Sparganothis* spp. |
| CrylA(a) | *Spodoptera* spp. |
| CrylA(a) | *Tortrix* spp. |
| CrylA(a) | *Trichoplusia ni* |
| CrylA(a) | *Agriotes* spp. |
| CrylA(a) | *Anthonomus grandis* |
| CrylA(a) | *Curculio* spp. |
| CrylA(a) | *Diabrotica balteata* |
| CrylA(a) | *Leptinotarsa* spp. |

TABLE 2-continued

| AP | Control of |
|---|---|
| CrylA(a) | *Lissorhoptrus* spp. |
| CrylA(a) | *Otiorhynchus* spp. |
| CrylA(a) | *Aleurothrixus* spp. |
| CrylA(a) | *Aleyrodes* spp. |
| CrylA(a) | *Aonidiella* spp. |
| CrylA(a) | *Aphididea* spp. |
| CrylA(a) | *Aphis* spp. |
| CrylA(a) | *Bemisia tabaci* |
| CrylA(a) | *Empoasca* spp. |
| CrylA(a) | *Mycus* spp. |
| CrylA(a) | *Nephotettix* spp. |
| CrylA(a) | *Nilaparvata* spp. |
| CrylA(a) | *Pseudococcus* spp. |
| CrylA(a) | *Psylla* spp. |
| CrylA(a) | *Quadraspidiotus* spp. |
| CrylA(a) | *Schizaphis* spp. |
| CrylA(a) | *Trialeurodes* spp. |
| CrylA(a) | *Lyriomyza* spp. |
| CrylA(a) | *Oscinella* spp. |
| CrylA(a) | *Phorbia* spp. |
| CrylA(a) | *Frankliniella* spp. |
| CrylA(a) | *Thrips* spp. |
| CrylA(a) | *Scirtothrips aurantii* |
| CrylA(a) | *Aceria* spp. |
| CrylA(a) | *Aculus* spp. |
| CrylA(a) | *Brevipaipus* spp. |
| CrylA(a) | *Panonychus* spp. |
| CrylA(a) | *Phyllocoptruta* spp. |
| CrylA(a) | *Tetranychus* spp. |
| CrylA(a) | *Heterodera* spp. |
| CrylA(a) | *Meloidogyne* spp. |
| CrylA(b) | *Adoxophyes* spp. |
| CrylA(b) | *Agrotis* spp. |
| CrylA(b) | *Alabama argillaceae* |

TABLE 2-continued

| AP | Control of |
|---|---|
| CryIA(b) | *Anticarsia gemmatalis* |
| CryIA(b) | *Chilo* spp. |
| CryIA(b) | *Ciysia ambiguella* |
| CryIA(b) | *Crocidolomia binotaiis* |
| CryIA(b) | *Cydia* spp. |
| CryIA(b) | *Diparopsis castanea* |
| CryIA(b) | *Earias* spp. |
| CryIA(b) | *Ephestia* spp. |
| CryIA(b) | *Heliothis* spp. |
| CryIA(b) | *Hellula undalis* |
| CryIA(b) | *Keiferia lycopersicella* |
| CryIA(b) | *Leucoptera scitella* |
| CryIA(b) | *Lithocollethis* spp. |
| CryIA(b) | *Lobesia botrana* |
| CryIA(b) | *Ostrinia nubilalis* |
| CryIA(b) | *Pandemis* spp. |
| CryIA(b) | *Pectinophora gossyp.* |
| CryIA(b) | *Phyllocnistis citrella* |
| CryIA(b) | *Pieris* spp. |
| CryIA(b) | *Plutelia xyiostella* |
| CryIA(b) | *Scirpophaga* spp. |
| CryIA(b) | *Sesamia* spp. |
| CryIA(b) | *Sparganothis* spp. |
| CryIA(b) | *Spodoptera* spp. |
| CryIA(b) | *Tortrix* spp. |
| CryIA(b) | *Trichoplusia ni* |
| CryIA(b) | *Agriotes* spp. |
| CryIA(b) | *Anthonomus grandis* |
| CryIA(b) | *Curculio* spp. |
| CryIA(b) | *Diabrotica balteata* |
| CryIA(b) | *Leptinotarsa* spp. |
| CryIA(b) | *Lissorhoptrus* spp. |
| CryIA(b) | *Otiorhynchus* spp. |
| CryIA(b) | *Aleurothrixus* spp. |
| CryIA(b) | *Aleyrodes* spp. |
| CryIA(b) | *Aonidiella* spp. |
| CryIA(b) | *Aphididae* spp. |
| CryIA(b) | *Aphis* spp. |
| CryIA(b) | *Bemisia tabaci* |
| CryIA(b) | *Empoasca* spp. |
| CryIA(b) | *Mycus* spp. |
| CryIA(b) | *Nephotettix* spp. |
| CryIA(b) | *Nilaparvata* spp. |
| CryIA(b) | *Pseudococcus* spp. |
| CryIA(b) | *Psylla* spp. |
| CryIA(b) | *Quadraspidiotus* spp. |
| CryIA(b) | *Schizaphis* spp. |
| CryIA(b) | *Trialeurodes* spp. |
| CryIA(b) | *Lyriomyza* spp. |
| CryIA(b) | *Oscinella* spp. |
| CryIA(b) | *Phorbia* spp. |
| CryIA(b) | *Frankliniella* spp. |
| CryIA(b) | *Thrips* spp. |
| CryIA(b) | *Scirtothrips aurantii* |
| CryIA(b) | *Aceria* spp. |
| CryIA(b) | *Aculus* spp. |
| CryIA(b) | *Brevipalpus* spp. |
| CryIA(b) | *Panonychus* spp. |
| CryIA(b) | *Phyllocoptruta* spp. |
| CryIA(b) | *Tetranychus* spp. |
| CryIA(b) | *Heterodera* spp. |
| CryIA(b) | *Meloidogyne* spp. |
| CryIA(c) | *Adoxophyes* spp. |
| CryIA(c) | *Agrotis* spp. |
| CryIA(c) | *Alabama argillaceae* |
| CryIA(c) | *Anticarsia gemmatalis* |
| CryIA(c) | *Chilo* spp. |
| CryIA(c) | *Ciysia ambiguella* |
| CryIA(c) | *Crocidolomia binotalis* |
| CryIA(c) | *Cydia* spp. |
| CryIA(c) | *Diparopsis castanea* |
| CryIA(c) | *Earias* spp. |
| CryIA(c) | *Ephestia* spp. |
| CryIA(c) | *Heliothis* spp. |
| CryIA(c) | *Hellula undalis* |
| CryIA(c) | *Keiferia lycopersicella* |
| CryIA(c) | *Leucoptera scitella* |
| CryIA(c) | *Lithocollethis* spp. |

TABLE 2-continued

| AP | Control of |
|---|---|
| CryIA(c) | *Lobesia botrana* |
| CryIA(c) | *Ostrinia nubilalis* |
| CryIA(c) | *Pandemis* spp. |
| CryIA(c) | *Pectinophora gossypielia.* |
| CryIA(c) | *Phyllocnistis citrella* |
| CryIA(c) | *Pieris* spp. |
| CryIA(c) | *Plutella xyiostella* |
| CryIA(c) | *Scirpophaga* spp. |
| CryIA(c) | *Sesamia* spp. |
| CryIA(c) | *Sparganothis* spp. |
| CryIA(c) | *Spodoptera* spp. |
| CryIA(c) | *Tortrix* spp. |
| CryIA(c) | *Trichoplusia ni* |
| CryIA(c) | *Agriotes* spp. |
| CryIA(c) | *Anthonomus grandis* |
| CryIA(c) | *Curculio* spp. |
| CryIA(c) | *Diabrotica baiteata* |
| CryIA(c) | *Leptinotarsa* spp. |
| CryIA(c) | *Lissorhoptrus* spp. |
| CryIA(c) | *Otiorhynchus* spp. |
| CryIA(c) | *Aleurothrixus* spp. |
| CryIA(c) | *Aleyrodes* spp. |
| CryIA(c) | *Aonidiella* spp. |
| CryIA(c) | *Aphididae* spp. |
| CryIA(c) | *Aphis* spp. |
| CryIA(c) | *Bemisia tabaci* |
| CryIA(c) | *Empoasca* spp. |
| CryIA(c) | *Mycus* spp. |
| CryIA(c) | *Nephotettix* spp. |
| CryIA(c) | *Nilaparvata* spp. |
| CryIA(c) | *Pseudococcus* spp. |
| CryIA(c) | *Psylla* spp. |
| CryIA(c) | *Quadraspidiotus* spp. |
| CryIA(c) | *Schizaphis* spp. |
| CryIA(c) | *Trialeurodes* spp. |
| CryIA(c) | *Lyriomyza* spp. |
| CryIA(c) | *Oscinelia* spp. |
| CryIA(c) | *Phorbia* spp. |
| CryIA(c) | *Frankliniella* spp. |
| CryIA(c) | *Thrips* spp. |
| CryIA(c) | *Scirtothrips aurantii* |
| CryIA(c) | *Aceria* spp. |
| CryIA(c) | *Aculus* spp. |
| CryIA(c) | *Brevipalpus* spp. |
| CryIA(c) | *Panonychus* spp. |
| CryIA(c) | *Phyllocoptruta* spp. |
| CryIA(c) | *Tetranychus* spp. |
| CryIA(c) | *Heterodera* spp. |
| CryIA(c) | *Meloidogyne* spp. |
| CryIIA | *Adoxophyes* spp. |
| CryIIA | *Agrotis* spp. |
| CryIIA | *Alabama argillaceae* |
| CryIIA | *Anticarsia gemmatalis* |
| CryIIA | *Chilo* spp. |
| CryIIA | *Clysia ambiguella* |
| CryIIA | *Crocidolomia binotalis* |
| CryIIA | *Cydia* spp. |
| CryIIA | *Diparopsis castanea* |
| CryIIA | *Earias* spp. |
| CryIIA | *Ephestia* spp. |
| CryIIA | *Heliothis* spp. |
| CryIIA | *Hellula undalis* |
| CryIIA | *Keiferia lycopersicella* |
| CryIIA | *Leucoptera scitella* |
| CryIIA | *Lithocolliethis* spp. |
| CryIIA | *Lobesia botrana* |
| CryIIA | *Ostrinia nubilalis* |
| CryIIA | *Pandemis* spp. |
| CryIIA | *Pectinophora gossyp.* |
| CryIIA | *Phyllocnistis citrella* |
| CryIIA | *Pieris* spp. |
| CryIIA | *Plutella xylostella* |
| CryIIA | *Scirpophaga* spp. |
| CryIIA | *Sesamia* spp. |
| CryIIA | *Sparganothis* spp. |
| CryIIA | *Spodoptera* spp. |
| CryIIA | *Tortrix* spp. |
| CryIIA | *Trichoplusia ni* |

TABLE 2-continued

| AP | Control of |
|---|---|
| CryIIA | *Agriotes* spp. |
| CryIIA | *Anthonomus grandis* |
| CryIIA | *Curculio* spp. |
| CryIIA | *Diabrotica balteata* |
| CryIIA | *Leptinotarsa* spp. |
| CryIIA | *Lissorhoptrus* spp. |
| CryIIA | *Otiorhynchus* spp. |
| CryIIA | *Aleurothrixus* spp. |
| CryIIA | *Aleyrodes* spp. |
| CryIIA | *Aonidiella* spp. |
| CryIIA | *Aphididae* spp. |
| CryIIA | *Aphis* spp. |
| CryIIA | *Bemisia tabaci* |
| CryIIA | *Empoasca* spp. |
| CryIIA | *Mycus* spp. |
| CryIIA | *Nephotettix* spp. |
| CryIIA | *Nilaparvata* spp. |
| CryIIA | *Pseudococcus* spp. |
| CryIIA | *Psyila* spp. |
| CryIIA | *Quadraspidiotus* spp. |
| CryIIA | *Schizaphis* spp. |
| CryIIA | *Trialeurodes* spp. |
| CryIIA | *Lyriomyza* spp. |
| CryIIA | *Oscinella* spp. |
| CryIIA | *Phorbia* spp. |
| CryIIA | *Frankliniella* spp. |
| CryIIA | *Thrips* spp. |
| CryIIA | *Scirtothrips aurantii* |
| CryIIA | *Aceria* spp. |
| CryIIA | *Acutus* spp. |
| CryIIA | *Brevipalpus* spp. |
| CryIIA | *Panonychus* spp. |
| CryIIA | *Phyllocoptruta* spp. |
| CryIIA | *Tetranychus* spp. |
| CryIIA | *Heterodera* spp. |
| CryIIA | *Meloidogyne* spp. |
| CryIIIA | *Adoxophyes* spp. |
| CryIIIA | *Agrotis* spp. |
| CryIIIA | *Alabama argiiiaceae* |
| CryIIIA | *Anticarsia gemmataiis* |
| CryIIIA | *Chilo* spp. |
| CryIIIA | *Ciysia ambiguelia* |
| CryIIIA | *Crocodolomia binotalis* |
| CryIIIA | *Cydia* spp. |
| CryIIIA | *Diparopsis castanea* |
| CryIIIA | *Earias* spp. |
| CryIIIA | *Ephestia* spp. |
| CryIIIA | *Heliothis* spp. |
| CryIIIA | *Hellula undalis* |
| CryIIIA | *Keiferia lycopersicella* |
| CryIIIA | *Leucoptera scitella* |
| CryIIIA | *Lithocollethis* spp. |
| CryIIIA | *Lobesia botrana* |
| CryIIIA | *Ostrinia nubilalis* |
| CryIIIA | *Pandemis* spp. |
| CryIIIA | *Pectinophora gossyp.* |
| CryIIIA | *Phyllocnistis citrella* |
| CryIIIA | *Pieris* spp. |
| CryIIIA | *Plutella xylostella* |
| CryIIIA | *Scirpophaga* spp. |
| CryIIIA | *Sesamia* spp. |
| CryIIIA | *Sparganothis* spp. |
| CryIIIA | *Spodoptera* spp. |
| CryIIIA | *Tortrix* spp. |
| CryIIIA | *Trichoplusia ni* |
| CryIIIA | *Agriotes* spp. |
| CryIIIA | *Anthonomus grandis* |
| CryIIIA | *Curculio* spp. |
| CryIIIA | *Diabrotica balteata* |
| CryIIIA | *Leptinotarsa* spp. |
| CryIIIA | *Lissorhoptrus* spp. |
| CryIIIA | *Otiorhynchus* spp. |
| CryIIIA | *Aleurothrixus* spp. |
| CryIIIA | *Aleyrodes* spp. |
| CryIIIA | *Aonidiella* spp. |
| CryIIIA | *Aphididae* spp. |
| CryIIIA | *Aphis* spp. |
| CryIIIA | *Bemisia tabaci* |

TABLE 2-continued

| AP | Control of |
|---|---|
| CryIIIA | *Empoasca* spp. |
| CryIIIA | *Mycus* spp. |
| CryIIIA | *Nephotettix* spp. |
| CryIIIA | *Nilaparvata* spp. |
| CryIIIA | *Pseudococcus* spp. |
| CryIIIA | *Psylla* spp. |
| CryIIIA | *Quadraspidiotus* spp. |
| CryIIIA | *Schizaphis* spp. |
| CryIIIA | *Trialeurodes* spp. |
| CryIIIA | *Lyriomyza* spp. |
| CryIIIA | *Oscinella* spp. |
| CryIIIA | *Phorbia* spp. |
| CryIIIA | *Frankliniella* spp. |
| CryIIIA | *Thrips* spp. |
| CryIIIA | *Scirtothrips aurantii* |
| CryIIIA | *Aceria* spp. |
| CryIIIA | *Aculus* spp. |
| CryIIIA | *Brevipalpus* spp. |
| CryIIIA | *Panonychus* spp. |
| CryIIIA | *Phyllocoptruta* spp. |
| CryIIIA | *Tetranychus* spp. |
| CryIIIA | *Heterodera* spp. |
| CryIIIA | *Meloidogyne* spp. |
| CryIIIB2 | *Adoxophyes* spp. |
| CryIIIB2 | *Agrotis* spp. |
| CryIIIB2 | *Alabama argiilaceae* |
| CryIIIB2 | *Anticarsia gemmatalis* |
| CryIIIB2 | *Chilo* spp. |
| CryIIIB2 | *Clysia ambiguella* |
| CryIIIB2 | *Crocidolomia binotaiis* |
| CryIIIB2 | *Cydia* spp. |
| CryIIIB2 | *Diparopsis castanea* |
| CryIIIB2 | *Earias* spp. |
| CryIIIB2 | *Ephestia* spp. |
| CryIIIB2 | *Heliothis* spp. |
| CryIIIB2 | *Hellula undalis* |
| CryIIIB2 | *Keiferia lycopersicella* |
| CryIIIB2 | *Leucoptera sectelia* |
| CryIIIB2 | *Lithocollethis* spp. |
| CryIIIB2 | *Lobesia botrana* |
| CryIIIB2 | *Ostrinia nubilalis* |
| CryIIIB2 | *Pandemis* spp. |
| CryIIIB2 | *Pectinophora gossyp.* |
| CryIIIB2 | *Phyllocnistis citrella* |
| CryIIIB2 | *Pieris* spp. |
| CryIIIB2 | *Plutella xylostella* |
| CryIIIB2 | *Scirpophaga* spp. |
| CryIIIB2 | *Sesamia* spp. |
| CryIIIB2 | *Sparganothis* spp. |
| CryIIIB2 | *Spodoptera* spp. |
| CryIIIB2 | *Tortrix* spp. |
| CryIIIB2 | *Trichoplusia ni* |
| CryIIIB2 | *Agriotes* spp. |
| CryIIIB2 | *Anthonomus grandis* |
| CryIIIB2 | *Curculio* spp. |
| CryIIIB2 | *Diabrotica balteata* |
| CryIIIB2 | *Leptinotarsa* spp. |
| CryIIIB2 | *Lissorhoptrus* spp. |
| CryIIIB2 | *Otiorhynchus* spp. |
| CryIIIB2 | *Aleurothrixus* spp. |
| CryIIIB2 | *Aleyrodes* spp. |
| CryIIIB2 | *Aonidiella* spp. |
| CryIIIB2 | *Aphididae* spp. |
| CryIIIB2 | *Aphis* spp. |
| CryIIIB2 | *Bemisia tabaci* |
| CryIIIB2 | *Empoasca* spp. |
| CryIIIB2 | *Mycus* spp. |
| CryIIIB2 | *Nephotettix* spp. |
| CryIIIB2 | *Nilaparvata* spp. |
| CryIIIB2 | *Pseudococcus* spp. |
| CryIIIB2 | *Psylla* spp. |
| CryIIIB2 | *Quadraspidiotus* spp. |
| CryIIIB2 | *Schizaphis* spp. |
| CryIIIB2 | *Trialeurodes* spp. |
| CryIIIB2 | *Lyriomyza* spp. |
| CryIIIB2 | *Oscinella* spp. |
| CryIIIB2 | *Phorbia* spp. |
| CryIIIB2 | *Frankliniella* spp. |

TABLE 2-continued

| AP | Control of |
|---|---|
| CryIIIB2 | *Thrips* spp. |
| CryIIIB2 | *Scirtothrips aurantii* |
| CryIIIB2 | *Aceria* spp. |
| CryIIIB2 | *Acutus* spp. |
| CryIIIB2 | *Brevipalpus* spp. |
| CryIIIB2 | *Panonychus* spp. |
| CryIIIB2 | *Phyllocoptruta* spp. |
| CryIIIB2 | *Tetranychus* spp. |
| CryIIIB2 | *Heterodera* spp. |
| CryIIIB2 | *Meloidogyne* spp. |
| CytA | *Adoxophyes* spp. |
| CytA | *Agrotis* spp. |
| CytA | *Alabama argiilaceae* |
| CytA | *Anticarsia gemmatalis* |
| CytA | *Chilo* spp. |
| CytA | *Clysia ambiguella* |
| CytA | *Crocidolomia binotaiis* |
| CytA | *Cydia* spp. |
| CytA | *Diparopsis castanea* |
| CytA | *Earias* spp. |
| CytA | *Ephestia* spp. |
| CytA | *Heliothis* spp. |
| CytA | *Hellula undalis* |
| CytA | *Keiferia lycopersicella* |
| CytA | *Leucoptera scitelia* |
| CytA | *Lithocollethis* spp. |
| CytA | *Lobesia botrana* |
| CytA | *Ostrinia nubilalis* |
| CytA | *Pandemis* spp. |
| CytA | *Pectinophora gossyp.* |
| CytA | *Phyllocnistis citrella* |
| CytA | *Pieris* spp. |
| CytA | *Plutella xylostella* |
| CytA | *Scirpophaga* spp. |
| CytA | *Sesamia* spp. |
| CytA | *Sparganothis* spp. |
| CytA | *Spodoptera* spp. |
| CytA | *Tortrix* spp. |
| CytA | *Trichoplusia ni* |
| CytA | *Agriotes* spp. |
| CytA | *Anthonomus grandis* |
| CytA | *Curculio* spp. |
| CytA | *Diabrotica balteata* |
| CytA | *Leptinotarsa* spp. |
| CytA | *Lissorhoptrus* spp. |
| CytA | *Otiorhynchus* spp. |
| CytA | *Aleurothrixus* spp. |
| CytA | *Aleyrodes* spp. |
| CytA | *Aonidielia* spp. |
| CytA | *Aphididae* spp. |
| CytA | *Aphis* spp. |
| CytA | *Bemisia tabaci* |
| CytA | *Empoasca* spp. |
| CytA | *Mycus* spp. |
| CytA | *Nephotettix* spp. |
| CytA | *Nilaparvata* spp. |
| CytA | *Pseudococcus* spp. |
| CytA | *Psylla* spp. |
| CytA | *Quadraspidiotus* spp. |
| CytA | *Schizaphis* spp. |
| CytA | *Trialeurodes* spp. |
| CytA | *Lyriomyza* spp. |
| CytA | *Oscinella* spp. |
| CytA | *Phorbia* spp. |
| CytA | *Frankliniella* spp. |
| CytA | *Thrips* spp. |
| CytA | *Scirtothrips aurantii* |
| CytA | *Aceria* spp. |
| CytA | *Acutus* spp. |
| CytA | *Brevipalpus* spp. |
| CytA | *Panonychus* spp. |
| CytA | *Phyllocoptruta* spp. |
| CytA | *Tetranychus* spp. |
| CytA | *Heterodera* spp. |
| CytA | *Meloidogyne* spp. |
| VIP3 | *Adoxophyes* spp. |
| VIP3 | *Agrotis* spp. |
| VIP3 | *Alabama argillaceae* |

TABLE 2-continued

| AP | Control of |
|---|---|
| VIP3 | *Anticarsia gemmatalis* |
| VIP3 | *Chilo* spp. |
| VIP3 | *Clysia ambiguella* |
| VIP3 | *Crocidolomia binotalis* |
| VIP3 | *Cydia* spp. |
| VIP3 | *Diparopsis castanea* |
| VIP3 | *Earias* spp. |
| VIP3 | *Ephestia* spp. |
| VIP3 | *Heliothis* spp. |
| VIP3 | *Hellula undalis* |
| VIP3 | *Keiferia lycopersicella* |
| VIP3 | *Leucoptera scitella* |
| VIP3 | *Lithocollethis* spp. |
| VIP3 | *Lobesia botrana* |
| VIP3 | *Ostrinia nubilalis* |
| VIP3 | *Pandemis* spp. |
| VIP3 | *Pectinophora gossyp.* |
| VIP3 | *Phyllocnistis citrella* |
| VIP3 | *Pieris* spp. |
| VIP3 | *Piutella xylostella* |
| VIP3 | *Scirpophaga* spp. |
| VIP3 | *Sesamia* spp. |
| VIP3 | *Sparganothis* spp. |
| VIP3 | *Spodoptera* spp. |
| VIP3 | *Tortrix* spp. |
| VIP3 | *Trichoplusia ni* |
| VIP3 | *Agriotes* spp. |
| VIP3 | *Anthonomus grandis* |
| VIP3 | *Curculio* spp. |
| VIP3 | *Diabrotica balteata* |
| VIP3 | *Leptinotarsa* spp. |
| VIP3 | *Lissorhoptrus* spp. |
| VIP3 | *Otiorhynchus* spp. |
| VIP3 | *Aleurothrixus* spp. |
| VIP3 | *Aleyrodes* spp. |
| VIP3 | *Aonidiella* spp. |
| VIP3 | *Aphididae* spp. |
| VIP3 | *Aphis* spp. |
| VIP3 | *Bemisia tabaci* |
| VIP3 | *Empoasca* spp. |
| VIP3 | *Mycus* spp. |
| VIP3 | *Nephotettix* spp. |
| VIP3 | *Niiaparvata* spp. |
| VIP3 | *Pseudococcus* spp. |
| VIP3 | *Psylla* spp. |
| VIP3 | *Quadraspidiotus* spp. |
| VIP3 | *Schizaphis* spp. |
| VIP3 | *Trialeurodes* spp. |
| VIP3 | *Lyriomyza* spp. |
| VIP3 | *Oscinella* spp. |
| VIP3 | *Phorbia* spp. |
| VIP3 | *Frankliniella* spp. |
| VIP3 | *Thrips* spp. |
| VIP3 | *Scirtothrips aurantii* |
| VIP3 | *Aceria* spp. |
| VIP3 | *Acutus* spp. |
| VIP3 | *Brevipalpus* spp. |
| VIP3 | *Panonychus* spp. |
| VIP3 | *Phyllocoptruta* spp. |
| VIP3 | *Tetranychus* spp. |
| VIP3 | *Heterodera* spp. |
| VIP3 | *Meloidogyne* spp. |
| GL | *Adoxophyes* spp. |
| GL | *Agrotis* spp. |
| GL | *Alabama argillaceae* |
| GL | *Anticarsia gemmatalis* |
| GL | *Chilo* spp. |
| GL | *Clysia ambiguella* |
| GL | *Crocidolomia binotaiis* |
| GL | *Cydia* spp. |
| GL | *Diparopsis castanea* |
| GL | *Earias* spp. |
| GL | *Ephestia* spp. |
| GL | *Heliothis* spp. |
| GL | *Hellula undalis* |
| GL | *Keiferia lycopersicella* |
| GL | *Leucoptera scitella* |

TABLE 2-continued

| AP | Control of |
|---|---|
| GL | *Lithocollethis* spp. |
| GL | *Lobesia botrana* |
| GL | *Ostrinia nubilalis* |
| GL | *Pandemis* spp. |
| GL | *Pectinophora gossyp.* |
| GL | *Phyliocnistis citrella* |
| GL | *Pieris* spp. |
| GL | *Plutella xylostella* |
| GL | *Scirpophaga* spp. |
| GL | *Sesamia* spp. |
| GL | *Sparganothis* spp. |
| GL | *Spodoptera* spp. |
| GL | *Tortrix* spp. |
| GL | *Trichoplusia ni* |
| GL | *Agriotes* spp. |
| GL | *Anthonomus grandis* |
| GL | *Curculio* spp. |
| GL | *Diabrotica balteata* |
| GL | *Leptinotarsa* spp. |
| GL | *Lissorhoptrus* spp. |
| GL | *Otiorhynchus* spp. |
| GL | *Aleurothrixus* spp. |
| GL | *Aleyrodes* spp. |
| GL | *Aonidiella* spp. |
| GL | *Aphididae* spp. |
| GL | *Aphis* spp. |
| GL | *Bemisia tabaci* |
| GL | *Empoasca* spp. |
| GL | *Mycus* spp. |
| GL | *Nephotettix* spp. |
| GL | *Nilaparvata* spp. |
| GL | *Pseudococcus* spp. |
| GL | *Psylia* spp. |
| GL | *Quadraspidiotus* spp. |
| GL | *Schizaphis* spp. |
| GL | *Trialeurodes* spp. |
| GL | *Lyriomyza* spp. |
| GL | *Oscinella* spp. |
| GL | *Phorbia* spp. |
| GL | *Frankliniella* spp. |
| GL | *Thrips* spp. |
| GL | *Scirtothrips aurantii* |
| GL | *Aceria* spp. |
| GL | *Aculus* spp. |
| GL | *Brevipalpus* spp. |
| GL | *Panonychus* spp. |
| GL | *Phyliocoptruta* spp. |
| GL | *Tetranychus* spp. |
| GL | *Heterodera* spp. |
| GL | *Meioidogyne* spp. |
| PL | *Adoxophyesspp.* |
| PL | *Agrotis* spp. |
| PL | *Alabama argillaceae* |
| PL | *Anticarsia gemmatalis* |
| PL | *Chilo* spp. |
| PL | *Clysia ambiguella* |
| PL | *Crocidolomia binotalis* |
| PL | *Cydia* spp. |
| PL | *Diparopsis castanea* |
| PL | *Earias* spp. |
| PL | *Ephestia* spp. |
| PL | *Heliothis* spp. |
| PL | *Hellula undaiis* |
| PL | *Keiferia lycopersicella* |
| PL | *Leucoptera scitella* |
| PL | *Lithocollethis* spp. |
| PL | *Lobesia botrana* |
| PL | *Ostrinia nubilalis* |
| PL | *Pandemis* spp. |
| PL | *Pectinophora gossyp.* |
| PL | *Phyllocnistis citrella* |
| PL | *Pieris* spp. |
| PL | *Plutella xylostella* |
| PL | *Scirpophaga* spp. |
| PL | *Sesamia* spp. |
| PL | *Sparganothis* spp. |
| PL | *Spodoptera* spp. |
| PL | *Tortrix* spp. |

TABLE 2-continued

| AP | Control of |
|---|---|
| PL | *Trichoplusia ni* |
| PL | *Agriotes* spp. |
| PL | *Anthonomus grandis* |
| PL | *Curculio* spp. |
| PL | *Diabrotica balteata* |
| PL | *Leptinotarsa* spp. |
| PL | *Lissorhoptrus* spp. |
| PL | *Otiorhynchus* spp. |
| PL | *Aleurothrixus* spp. |
| PL | *Aleyrodes* spp. |
| PL | *Aonidiella* spp. |
| PL | *Aphididae* spp. |
| PL | *Aphis* spp. |
| PL | *Bemisia tabaci* |
| PL | *Empoasca* spp. |
| PL | *Mycus* spp. |
| PL | *Nephotettix* spp. |
| PL | *Nilaparvata* spp. |
| PL | *Pseudococcus* spp. |
| PL | *Psylla* spp. |
| PL | *Quadraspidiotus* spp. |
| PL | *Schizaphis* spp. |
| PL | *Trialeurodes* spp. |
| PL | *Lyriomyza* spp. |
| PL | *Oscinella* spp. |
| PL | *Phorbia* spp. |
| PL | *Frankliniella* spp. |
| PL | *Thrips* spp. |
| PL | *Scirtothrips auranii* |
| PL | *Aceria* spp. |
| PL | *Aculus* spp. |
| PL | *Brevipalpus* spp. |
| PL | *Panonychus* spp. |
| PL | *Phyllocoptruta* spp. |
| PL | *Tetranychus* spp. |
| PL | *Heterodera* spp. |
| PL | *Meloidogyne* spp. |
| XN | *Adoxophyes* spp. |
| XN | *Agrotis* spp. |
| XN | *Alabama argiliaceae* |
| XN | *Anticarsia gemmatalis* |
| XN | *Chilo* spp. |
| XN | *Clysia ambiguella* |
| XN | *Crocidolomia binotalis* |
| XN | *Cydia* spp. |
| XN | *Diparopsis castanea* |
| XN | *Earias* spp. |
| XN | *Ephestia* spp. |
| XN | *Heliothis* spp. |
| XN | *Helluia undaiis* |
| XN | *Keiferia lycopersicella* |
| XN | *Leucoptera scitella* |
| XN | *Lithocollethis* spp. |
| XN | *Lobesia botrana* |
| XN | *Ostrinia nubilalis* |
| XN | *Pandemis* spp. |
| XN | *Pectinophora gossyp.* |
| XN | *Phyllocnistis citrella* |
| XN | *Pieris* spp. |
| XN | *Plutella xylostella* |
| XN | *Scirpophaga* spp. |
| XN | *Sesamia* spp. |
| XN | *Sparganothis* spp. |
| XN | *Spodoptera* spp. |
| XN | *Tortrix* spp. |
| XN | *Trichoplusia ni* |
| XN | *Agriotes* spp. |
| XN | *Anthonomus grandis* |
| XN | *Curculio* spp. |
| XN | *Diabrotica balteata* |
| XN | *Leptinotarsa* spp. |
| XN | *Lissorhoptrus* spp. |
| XN | *Otiorhynchus* spp. |
| XN | *Aleurothrixus* spp. |
| XN | *Aleyrodes* spp. |
| XN | *Aonidiella* spp. |
| XN | *Aphididae* spp. |
| XN | *Aphis* spp. |

TABLE 2-continued

| AP | Control of |
|---|---|
| XN | *Bemisia tabaci* |
| XN | *Empoasca* spp. |
| XN | *Mycus* spp. |
| XN | *Nephotettix* spp. |
| XN | *Nilaparvata* spp. |
| XN | *Pseudococcus* spp. |
| XN | *Psylla* spp. |
| XN | *Quadraspidiotus* spp. |
| XN | *Schizaphis* spp. |
| XN | *Trialeurodes* spp. |
| XN | *Lyriomyza* spp. |
| XN | *Oscinella* spp. |
| XN | *Phorbia* spp. |
| XN | *Frankliniella* spp. |
| XN | *Thrips* spp. |
| XN | *Scirtothrips aurantii* |
| XN | *Aceria* spp. |
| XN | *Aculus* spp. |
| XN | *Brevipalpus* spp. |
| XN | *Panonychus* spp. |
| XN | *Phyllocoptruta* spp. |
| XN | *Tetranychus* spp. |
| XN | *Heterodera* spp. |
| XN | *Meloidogyne* spp. |
| Plnh. | *Adoxophyes* spp. |
| Plnh. | *Agrotis* spp. |
| Plnh. | *Alabama argiliaceae* |
| Plnh. | *Anticarsia gemmatalis* |
| Plnh. | *Chilo* spp. |
| Plnh. | *Clysia ambiguella* |
| Plnh. | *Crocidolomia binotalis* |
| Plnh. | *Cydia* spp. |
| Plnh. | *Diparopsis castanea* |
| Plnh. | *Earias* spp. |
| Plnh. | *Ephestia* spp. |
| Plnh. | *Heliothis* spp. |
| Plnh. | *Heliuia undalis* |
| Plnh. | *Keiferia lycopersicella* |
| Plnh. | *Leucoptera scitella* |
| Plnh. | *Lithocollethis* spp. |
| Plnh. | *Lobesia botrana* |
| Plnh. | *Ostrinia nubilalis* |
| Plnh. | *Pandemis* spp. |
| Plnh. | *Pectinophora gossyp.* |
| Plnh. | *Phyllocnistis citrelia* |
| Plnh. | *Pieris* spp. |
| Plnh. | *Plutella xylostella* |
| Plnh. | *Scirpophaga* spp. |
| Plnh. | *Sesamia* spp. |
| Plnh. | *Sparganothis* spp. |
| Plnh. | *Spodoptera* spp. |
| Plnh. | *Tortrix* spp. |
| Plnh. | *Trichoplusia ni* |
| Plnh. | *Agriotes* spp. |
| Plnh. | *Anthonomus grandis* |
| Plnh. | *Curculio* spp. |
| Plnh. | *Diabrotica balteata* |
| Plnh. | *Leptinotarsa* spp. |
| Plnh. | *Lissorhoptrus* spp. |
| Plnh. | *Otiorhynchus* spp. |
| Plnh. | *Aleurothrixus* spp. |
| Plnh. | *Aleyrodes* spp. |
| Plnh. | *Aonidiella* spp. |
| Plnh. | *Aphididae* spp. |
| Plnh. | *Aphis* spp. |
| Plnh. | *Bemisia tabaci* |
| Plnh. | *Empoasca* spp. |
| Plnh. | *Mycus* spp. |
| Plnh. | *Nephotettix* spp. |
| Plnh. | *Nilaparvata* spp. |
| Plnh. | *Pseudococcus* spp. |
| Plnh. | *Psylla* spp. |
| Plnh. | *Quadraspidiotus* spp. |
| Plnh. | *Schizaphis* spp. |
| Plnh. | *Trialeurodes* spp. |
| Plnh. | *Lyriomyza* spp. |
| Plnh. | *Oscinella* spp. |

TABLE 2-continued

| AP | Control of |
|---|---|
| Plnh. | *Phorbia* spp. |
| Plnh. | *Frankliniella* spp. |
| Plnh. | *Thrips* spp. |
| Plnh. | *Scirtothrips aurantii* |
| Plnh. | *Aceria* spp. |
| Plnh. | *Acutus* spp. |
| Plnh. | *Brevipalpus* spp. |
| Plnh. | *Panonychus* spp. |
| Plnh. | *Phyllocoptruta* spp. |
| Plnh. | *Tetranychus* spp. |
| Plnh. | *Heterodera* spp. |
| Plnh. | *Meloidogyne* spp. |
| PLec. | *Adoxophyes* spp. |
| PLec. | *Agrotis* spp. |
| PLec. | *Alabama argillaceae* |
| PLec. | *Anticarsia gemmatalis* |
| PLec. | *Chilo* spp. |
| PLec. | *Clysia ambiguella* |
| PLec. | *Crocidolomia binotalis* |
| PLec. | *Cydia* spp. |
| PLec. | *Diparopsis castanea* |
| PLec. | *Earias* spp. |
| PLec. | *Ephestia* spp. |
| PLec. | *Heliothis* spp. |
| PLec. | *Hellula undalis* |
| PLec. | *Keiferia lycopersicella* |
| PLec. | *Leucoptera scitella* |
| PLec. | *Lithocollethis* spp. |
| PLec. | *Lobesia botrana* |
| PLec. | *Ostrinia nubilalis* |
| PLec. | *Pandemis* spp. |
| PLec. | *Pectinophora gossyp.* |
| PLec. | *Phyllocnistis citrella* |
| PLec. | *Pieris* spp. |
| PLec. | *Plutella xylostella* |
| PLec. | *Scirpophaga* spp. |
| PLec. | *Sesamia* spp. |
| PLec. | *Sparganothis* spp. |
| PLec. | *Spodoptera* spp. |
| PLec. | *Tortrix* spp. |
| PLec. | *Trichoplusia ni* |
| PLec. | *Agriotes* spp. |
| PLec. | *Anthonomus grandis* |
| PLec. | *Curculio* spp. |
| PLec. | *Diabrotica balteata* |
| PLec. | *Leptinotarsa* spp. |
| PLec. | *Lissorhoptrus* spp. |
| PLec. | *Otiorhynchus* spp. |
| PLec. | *Aleurothrixus* spp. |
| PLec. | *Aleyrodes* spp. |
| PLec. | *Aonidiella* spp. |
| PLec. | *Aphididae* spp. |
| PLec. | *Aphis* spp. |
| PLec. | *Bemisia tabaci* |
| PLec. | *Empoasca* spp. |
| PLec. | *Mycus* spp. |
| PLec. | *Nephotettix* spp. |
| PLec. | *Nilaparvata* spp. |
| PLec. | *Pseudococcus* spp. |
| PLec. | *Psylia* spp. |
| PLec. | *Quadraspidiotus* spp. |
| PLec. | *Schizaphis* spp. |
| PLec. | *Trialeurodes* spp. |
| PLec. | *Lyriomyza* spp. |
| PLec. | *Oscinella* spp. |
| PLec. | *Phorbia* spp. |
| PLec. | *Frankliniella* spp. |
| PLec. | *Thrips* spp. |
| PLec. | *Scirtothnps aurantii* |
| PLec. | *Aceria* spp. |
| PLec. | *Aculus* spp. |
| PLec. | *Brevipalpus* spp. |
| PLec. | *Panonychus* spp. |
| PLec. | *Phyllocoptruta* spp. |
| PLec. | *Tetranychus* spp. |
| PLec. | *Heterodera* spp. |
| PLec. | *Meloidogyne* spp. |
| Aggl. | *Adoxophyes* spp. |

TABLE 2-continued

| AP | Control of |
|---|---|
| Aggl. | *Agrotis* spp. |
| Aggl. | *Alabama argillaceae* |
| Aggl. | *Anticarsia gemmatalis* |
| Aggl. | *Chilo* spp. |
| Aggl. | *Clysia ambiguella* |
| Aggl. | *Crocidolomia binotalis* |
| Aggl. | *Cydia* spp. |
| Aggl. | *Diparopsis castanea* |
| Aggl. | *Earias* spp. |
| Aggl. | *Ephestia* spp. |
| Aggl. | *Heliothis* spp. |
| Aggl. | *Hellula undalis* |
| Aggl. | *Keiferia lycopersicella* |
| Aggl. | *Leucoptera scitella* |
| Aggl. | *Lithocollethis* spp. |
| Aggl. | *Lobesia botrana* |
| Aggl. | *Ostrinia nubilalis* |
| Aggl. | *Pandemis* spp. |
| Aggl. | *Pectinophora gossyp.* |
| Aggl. | *Phyllocnistis citrella* |
| Aggl. | *Pieris* spp. |
| Aggl. | *Plutiia xylostella* |
| Aggl. | *Scirpophaga* spp. |
| Aggl. | *Sesamia* spp. |
| Aggl. | *Sparganothis* spp. |
| Aggl. | *Spodoptera* spp. |
| Aggl. | *Tortrix* spp. |
| Aggl. | *Trichoplusia ni* |
| Aggl. | *Agriotes* spp. |
| Aggl. | *Anthonomus grandis* |
| Aggl. | *Curculio* spp. |
| Aggl. | *Diabrotica balteata* |
| Aggl. | *Leptinotarsa* spp. |
| Aggl. | *Lissorhoptrus* spp. |
| Aggl. | *Otiorhynchus* spp. |
| Aggl. | *Aleurothrixus* spp. |
| Aggl. | *Aleyrodes* spp. |
| Aggl. | *Aonidiella* spp. |
| Aggl. | *Aphididae* spp. |
| Aggl. | *Aphis* spp. |
| Aggl. | *Bemisia tabaci* |
| Aggl. | *Empoasca* spp. |
| Aggl. | *Mycus* spp. |
| Aggl. | *Nephotettix* spp. |
| Aggl. | *Nilaparvata* spp. |
| Aggl. | *Pseudococcus* spp. |
| Aggl. | *Psylla* spp. |
| Aggl. | *Quadraspidiotus* spp. |
| Aggl. | *Schizaphis* spp. |
| Aggl. | *Trialeurodes* spp. |
| Aggl. | *Lyriomyza* spp. |
| Aggl. | *Oscinella* spp. |
| Aggl. | *Phorbia* spp. |
| Aggl. | *Frankliniella* spp. |
| Aggl. | *Thrips* spp. |
| Aggl. | *Scirtothrips auranti* |
| Aggl. | *Aceria* spp. |
| Aggl. | *Aculus* spp. |
| Aggl. | *Brevipalpus* spp. |
| Aggl. | *Panonychus* spp. |
| Aggl. | *Phyllocoptruta spp* |
| Aggl. | *Tetranychus* spp. |
| Aggl. | *Heterodera* spp. |
| Aggl. | *Meloidogyne* spp. |
| CO | *Adoxophyes* spp. |
| CO | *Agrotis* spp. |
| CO | *Alabama argiliaceae* |
| CO | *Anticarsia gemmatalis* |
| CO | *Chilo* spp. |
| CO | *Ciysia ambiguella* |
| CO | *Crocidolomia binotalis* |
| CO | *Cydia* spp. |
| CO | *Diparopsis castanea* |
| CO | *Earias* spp. |
| CO | *Ephestia* spp. |
| CO | *Heliothis* spp. |
| CO | *Hellula undalis* |
| CO | *Keiferia lycopersicella* |
| CO | *Leucoptera scitella* |
| CO | *Lithocollethis* spp. |
| CO | *Lobesia botrana* |
| CO | *Ostrinia nubilalis* |
| CO | *Pandemis* spp. |
| CO | *Pectinophora gossyp.* |
| CO | *Phyllocnistis citrella* |
| CO | *Pieris* spp. |
| CO | *Plutella xylostella* |
| CO | *Scirpophaga* spp. |
| CO | *Sesamia* spp. |
| CO | *Sparganothis* spp. |
| CO | *Spodoptera* spp. |
| CO | *Tortrix* spp. |
| CO | *Trichoplusia ni* |
| CO | *Agriotes* spp. |
| CO | *Anthonomus grandis* |
| CO | *Curculio* spp. |
| CO | *Diabrotica balteata* |
| CO | *Leptinotarsa* spp. |
| CO | *Lissorhoptrus* spp. |
| CO | *Otiorhynchus* spp. |
| CO | *Aleurothrixus* spp. |
| CO | *Aleyrodes* spp. |
| CO | *Aonidielia* spp. |
| CO | *Aphididae* spp. |
| CO | *Aphis* spp. |
| CO | *Bemisia tabaci* |
| CO | *Empoasca* spp. |
| CO | *Mycus* spp. |
| CO | *Nephotettix* spp. |
| CO | *Nilaparvata* spp. |
| CO | *Pseudococcus* spp. |
| CO | *Psylla* spp. |
| CO | *Quadraspidiotus* spp. |
| CO | *Schizaphis* spp. |
| CO | *Trialeurodes* spp. |
| CO | *Lyriomyza* spp. |
| CO | *Oscinella* spp. |
| CO | *Phorbia* spp. |
| CO | *Frankliniella* spp. |
| CO | *Thrips* spp. |
| CO | *Scirtothrips aurantii* |
| CO | *Aceria* spp. |
| CO | *Acutus* spp. |
| CO | *Brevipalpus* spp. |
| CO | *Panonychus* spp. |
| CO | *Phyllocoptruta* spp. |
| CO | *Tetranychus* spp. |
| CO | *Heterodera* spp. |
| CO | *Meloidogyne* spp. |
| CH | *Adoxophyes* spp. |
| CH | *Agrotis* spp. |
| CH | *Alabama argillaceae* |
| CH | *Anticarsia gemmatalis* |
| CH | *Chilo* spp. |
| CH | *Clysia ambiguella* |
| CH | *Crocidolomia binotalis* |
| CH | *Cydia* spp. |
| CH | *Diparopsis castanea* |
| CH | *Earias* spp. |
| CH | *Ephestia* spp. |
| CH | *Heliothis* spp. |
| CH | *Hellula undalis* |
| CH | *Keiferia lycopersicella* |
| CH | *Leucoptera scitella* |
| CH | *Lithocollethis* spp. |
| CH | *Lobesia botrana* |
| CH | *Ostrinia nubilalis* |
| CH | *Pandemis* spp. |
| CH | *Pectinophora gossyp.* |
| CH | *Phyllocnistis citrella* |

TABLE 2-continued

| AP | Control of |
|---|---|
| CH | *Pieris* spp. |
| CH | *Plutella xylostella* |
| CH | *Scirpophaga* spp. |
| CH | *Sesamia* spp. |
| CH | *Sparganothis* spp. |
| CH | *Spodoptera* spp. |
| CH | *Tortrix* spp. |
| CH | *Trichoplusia ni* |
| CH | *Agriotes* spp. |
| CH | *Anthonomus grandis* |
| CH | *Curculio* spp. |
| CH | *Diabrotica balteata* |
| CH | *Leptinotarsa* spp. |
| CH | *Lissorhoptrus* spp. |
| CH | *Otiorhynohus* spp. |
| CH | *Aleurothrixus* spp. |
| CH | *Aleyrodes* spp. |
| CH | *Aonidiella* spp. |
| CH | *Aphididae* spp. |
| CH | *Aphis* spp. |
| CH | *Bemisia tabaci* |
| CH | *Empoasca* spp. |
| CH | *Mycus* spp. |
| CH | *Nephotettix* spp. |
| CH | *Nilaparvata* spp. |
| CH | *Pseudococcus* spp. |
| CH | *Psylla* spp. |
| CH | *Quadraspidiotus* spp. |
| CH | *Schizaphis* spp. |
| CH | *Trialeurodes* spp. |
| CH | *Lyriomyza* spp. |
| CH | *Oscinella* spp. |
| CH | *Phorbia* spp. |
| CH | *Frankliniella* spp. |
| CH | *Thrips* spp. |
| CH | *Scirtothrips aurantii* |
| CH | *Aceria* spp. |
| CH | *Aculus* spp. |
| CH | *Brevipalpus* spp. |
| CH | *Panonychus* spp. |
| CH | *Phyllocoptruta* spp. |
| CH | *Tetranychus* spp. |
| CH | *Heterodera* spp. |
| CH | *Meloidogyne* spp. |
| SS | *Adoxophyes* spp. |
| SS | *Agrotis* spp. |
| SS | *Alabama argillaceae* |
| SS | *Anticarsia gemmatalis* |
| SS | *Chilo* spp. |
| SS | *Clysia ambiguella* |
| SS | *Crocidolomia binotalis* |
| SS | *Cydia* spp. |
| SS | *Diparopsis castanea* |
| SS | *Earias* spp. |
| SS | *Ephestia* spp. |
| SS | *Heliothis* spp. |
| SS | *Hellula undalis* |
| SS | *Keiferia lycopersicella* |
| SS | *Leucoptera scitella* |
| SS | *Lithocollethis* spp. |
| SS | *Lobesia botrana* |
| SS | *Ostrinia nubilalis* |
| SS | *Pandemis* spp. |
| SS | *Pectinophora gossyp.* |
| SS | *Phyllocnistis citrella* |
| SS | *Pieris* spp. |
| SS | *Plutella xylostella* |
| SS | *Scirpophaga* spp. |
| SS | *Sesamia* spp. |
| SS | *Sparganothis* spp. |
| SS | *Spodoptera* spp. |
| SS | *Tortrix* spp. |
| SS | *Trichopiusia ni* |
| SS | *Agriotes* spp. |
| SS | *Anthonomus grandis* |
| SS | *Curculio* spp. |
| SS | *Diabrotica balteata* |

TABLE 2-continued

| AP | Control of |
|---|---|
| SS | *Leptinotarsa* spp. |
| SS | *Lissorhoptrus* spp. |
| SS | *Otiorhynchus* spp. |
| SS | *Aleurothrixus* spp. |
| SS | *Aleyrodes* spp. |
| SS | *Aonidielia* spp. |
| SS | *Aphididae* spp. |
| SS | *Aphis* spp. |
| SS | *Bemisia tabaci* |
| SS | *Empoasca* spp. |
| SS | *Mycus* spp. |
| SS | *Nephotettix* spp. |
| SS | *Nilaparvata* spp. |
| SS | *Pseudococcus* spp. |
| SS | *Psylla* spp. |
| SS | *Quadraspidiotus* spp. |
| SS | *Schizaphis* spp. |
| SS | *Trialeurodes* spp. |
| SS | *Lyriomyza* spp. |
| SS | *Oscinella* spp. |
| SS | *Phorbia* spp. |
| SS | *Frankliniella* spp. |
| SS | *Thrips* spp. |
| SS | *Scirtothrips aurantii* |
| SS | *Aceria* spp. |
| SS | *Aculus* spp. |
| SS | *Brevipalpus* spp. |
| SS | *Panonychus* spp. |
| SS | *Phyllocoptruta* spp. |
| SS | *Tetranychus* spp. |
| SS | *Heterodera* spp. |
| SS | *Meloidogyne* spp. |
| HO | *Adoxophyes* spp. |
| HO | *Agrotis* spp. |
| HO | *Alabama argillaceae* |
| HO | *Anticarsia gemmatalis* |
| HO | *Chilo* spp. |
| HO | *Clysia ambiguella* |
| HO | *Crocidolomia binotalis* |
| HO | *Cydia* spp. |
| HO | *Diparopsis castanea* |
| HO | *Earias* spp. |
| HO | *Ephestia* spp. |
| HO | *Heliothis* spp. |
| HO | *Hellula undalis* |
| HO | *Keiferia lycopersicella* |
| HO | *Leucoptera scitella* |
| HO | *Lithocollethis* spp. |
| HO | *Lobesia botrana* |
| HO | *Ostrinia nubilalis* |
| HO | *Pandemis* spp. |
| HO | *Pectinophora gossypiella* |
| HO | *Phyllocnistis citrella* |
| HO | *Pieris* spp. |
| HO | *Plutella xylostella* |
| HO | *Scirpophaga* spp. |
| HO | *Sesamia* spp. |
| HO | *Sparganothis* spp. |
| HO | *Spodoptera* spp. |
| HO | *Tortrix* spp. |
| HO | *Trichoplusia ni* |
| HO | *Agriotes* spp. |
| HO | *Anthonomus grandis* |
| HO | *Curculio* spp. |
| HO | *Diabrotica balteata* |
| HO | *Leptinotarsa* spp. |
| HO | *Lissorhoptrus* spp. |
| HO | *Otiorhynchus* spp. |
| HO | *Aleurothrixus* spp. |
| HO | *Aleyrodes* spp. |
| HO | *Aonidiella* spp. |
| HO | *Aphididae* spp. |
| HO | *Aphis* spp. |
| HO | *Bemisia tabaci* |
| HO | *Empoasca* spp. |
| HO | *Mycus* spp. |
| HO | *Nephotettix* spp. |
| HO | *Nilaparvata* spp. |

TABLE 2-continued

| AP | Control of |
|---|---|
| HO | *Pseudococcus* spp. |
| HO | *Psylla* spp. |
| HO | *Quadraspidiotus* spp. |
| HO | *Schizaphis* spp. |
| HO | *Trialeurodes* spp. |
| HO | *Lyriomyza* spp. |
| HO | *Oscinella* spp. |
| HO | *Phorbia* spp. |
| HO | *Frankliniella* spp. |
| HO | *Thrips* spp. |
| HO | *Scirtothrips aurantii* |
| HO | *Aceria* spp. |
| HO | *Acutus* spp. |
| HO | *Brevipalpus* spp. |
| HO | *Panonychus* spp. |
| HO | *Phyllocoptruta* spp. |
| HO | *Tetranychus* spp. |
| HO | *Heterodera* spp. |
| HO | *Meloidogyne* spp. |

In the table, the following abbreviations were used:
active principle of the transgenic plant: AP
*Photorhabdus* luminescens: PL
*Xenorhabdus nematophilus*: XN
proteinase inhibitors: PInh.
plant lectins PLec.
agglutinines: Aggl.
3-hydroxysteroid oxidase: HO
cholesterol oxidase: CO
chitinase: CH
glucanase: GL
stilbene synthase: SS

TABLE 3

| Principle | Tolerance to | Plant |
|---|---|---|
| ALS | sulphonylurea compounds etc.*** | cotton |
| ALS | sulphonylurea compounds etc.*** | rice |
| ALS | sulphonylurea compounds etc.*** | *Brassica* |
| ALS | sulphonylurea compounds etc.*** | potatoes |
| ALS | sulphonylurea compounds etc.*** | tomatoes |
| ALS | sulphonylurea compounds etc.*** | pumpkin |
| ALS | sulphonylurea compounds etc.*** | soya beans |
| ALS | sulphonylurea compounds etc.*** | maize |
| ALS | sulphonylurea compounds etc.*** | wheat |
| ALS | sulphonylurea compounds etc.*** | pome fruit |
| ALS | sulphonylurea compounds etc.*** | stone fruit |
| ALS | sulphonylurea compounds etc.*** | citrus fruit |
| ACCase | +++ | cotton |
| ACCase | +++ | rice |
| ACCase | +++ | *Brassica* |
| ACCase | +++ | potato |
| ACCase | +++ | tomatoes |
| ACCase | +++ | pumpkin |
| ACCase | +++ | soya beans |
| ACCase | +++ | maize |
| ACCase | +++ | wheat |
| ACCase | +++ | pome fruit |
| ACCase | +++ | stone fruit |
| ACCase | +++ | citrus fruit |
| HPPD | isoxaflutole, isoxachlortole, sulcotrione, mesotrione | cotton |
| HPPD | isoxaflutole, isoxachlortole, sulcotrione, mesotrione | rice |
| HPPD | isoxaflutole, isoxachlortole, sulcotrione, mesotrione | *Brassica* |
| HPPD | isoxaflutole, isoxachlortole, sulcotrione, mesotrione | potatoes |
| HPPD | isoxaflutole, isoxachlortole, sulcotrione, mesotrione | tomatoes |
| HPPD | isoxaflutole, isoxachlortole, sulcotrione, mesotrione | pumpkin |
| HPPD | isoxaflutole, isoxachlortole, sulcotrione, mesotrione | soya beans |

TABLE 3-continued

| Principle | Tolerance to | Plant |
|---|---|---|
| HPPD | isoxaflutole, isoxachlortole, sulcotrione, mesotrione | maize |
| HPPD | isoxaflutole, isoxachlortole, sulcotrione, mesotrione | wheat |
| HPPD | isoxaflutole, isoxachlortole, sulcotrione, mesotrione | pome fruit |
| HPPD | isoxaflutole, isoxachlortole, sulcotrione, mesotrione | stone fruit |
| HPPD | isoxaflutole, isoxachlortole, sulcotrione, mesotrione | citrus fruit |
| nitrilase | bromoxynil, loxynil | cotton |
| nitrilase | bromoxynil, loxynil | rice |
| nitrilase | bromoxynil, loxynil | *Brassica* |
| nitrilase | bromoxynil, loxynil | potatoes |
| nitrilase | bromoxynil, loxynil | tomatoes |
| nitrilase | bromoxynil, loxynil | pumpkin |
| nitrilase | bromoxynil, loxynil | soya beans |
| nitrilase | bromoxynil, loxynil | maize |
| nitrilase | bromoxynil, loxynil | wheat |
| nitrilase | bromoxynil, loxynil | pome fruit |
| nitrilase | bromoxynil, loxynil | stone fruit |
| nitrilase | bromoxynil, loxynil | citrus fruit |
| IPS | chloroactanilides &&& | cotton |
| IPS | chloroactanilides &&& | rice |
| IPS | chloroactanilides &&& | *Brassica* |
| IPS | chloroactanilides &&& | potatoes |
| IPS | chloroactanilides &&& | tomatoes |
| IPS | chloroactanilides &&& | pumpkin |
| IPS | chloroactanilides &&& | soya beans |
| IPS | chloroactanilides &&& | maize |
| IPS | chloroactanilides &&& | wheat |
| IPS | chloroactanilides &&& | pome fruit |
| IPS | chloroactanilides &&& | stone fruit |
| IPS | chloroactanilides &&& | citrus fruit |
| HOM | 2,4-D, mecoprop-P | cotton |
| HOM | 2,4-D, mecoprop-P | rice |
| HOM | 2,4-D, mecoprop-P | *Brassica* |
| HOM | 2,4-D, mecoprop-P | potatoes |
| HOM | 2,4-D, mecoprop-P | tomatoes |
| HOM | 2,4-D, mecoprop-P | pumpkin |
| HOM | 2,4-D, mecoprop-P | soya beans |
| HOM | 2,4-D, mecoprop-P | maize |
| HOM | 2,4-D, mecoprop-P | wheat |
| HOM | 2,4-D, mecoprop-P | pome fruit |
| HOM | 2,4-D, mecoprop-P | stone fruit |
| HOM | 2,4-D, mecoprop-P | citrus fruit |
| PROTOX | Protox inhibitors /// | cotton |
| PROTOX | Protox inhibitors /// | rice |
| PROTOX | Protox inhibitors /// | *Brassica* |
| PROTOX | Protox inhibitors /// | potatoes |
| PROTOX | Protox inhibitors /// | tomatoes |
| PROTOX | Protox inhibitors /// | pumpkin |
| PROTOX | Protox inhibitors /// | soya beans |
| PROTOX | Protox inhibitors /// | maize |
| PROTOX | Protox inhibitors /// | wheat |
| PROTOX | Protox inhibitors /// | pome fruit |
| PROTOX | Protox inhibitors /// | stone fruit |
| PROTOX | Protox inhibitors /// | citrus fruit |
| EPSPS | glyphosate and/or sulphosate | cotton |
| EPSPS | glyphosate and/or sulphosate | rice |
| EPSPS | glyphosate and/or sulphosate | *Brassica* |
| EPSPS | glyphosate and/or sulphosate | potatoes |
| EPSPS | glyphosate and/or sulphosate | tomatoes |
| EPSPS | glyphosate and/or sulphosate | pumpkin |
| EPSPS | glyphosate and/or sulphosate | soya beans |
| EPSPS | glyphosate and/or sulphosate | maize |
| EPSPS | glyphosate and/or sulphosate | wheat |
| EPSPS | glyphosate and/or sulphosate | pome fruit |
| EPSPS | glyphosate and/or sulphosate | stone fruit |
| EPSPS | glyphosate and/or sulphosate | citrus fruit |
| GS | gluphosinate and/or bialaphos | cotton |
| GS | gluphosinate and/or bialaphos | rice |
| GS | gluphosinate and/or bialaphos | *Brassica* |
| GS | gluphosinate and/or bialaphos | potatoes |
| GS | gluphosinate and/or bialaphos | tomatoes |
| GS | gluphosinate and/or bialaphos | pumpkin |
| GS | gluphosinate and/or bialaphos | soya beans |
| GS | gluphosinate and/or bialaphos | maize |

TABLE 3-continued

| Principle | Tolerance to | Plant |
|---|---|---|
| GS | gluphosinate and/or bialaphos | wheat |
| GS | gluphosinate and/or bialaphos | pome fruit |
| GS | gluphosinate and/or bialaphos | stone fruit |
| GS | gluphosinate and/or bialaphos | citrus fruit |

Abbreviations:

acetyl-CoA carboxylase: ACCase acetolactate synthase: ALS hydroxyphenylpyruvate dioxygenase: HPPD inhibition of protein synthesis: IPS hormone imitation: HO glutamine synthetase: GS protoporphyrinogen oxidase: PROTOX 5-enolpyruvyl-3-phosphoshikimate synthase: EPSPS TABLE 3-continued

| Principle | Tolerance to | Plant |
|---|---|---|

***included are sulphonylurea compounds, imidazolinones, triazolopyrimidines, dimethoxypyrimidines and N-acylsulphonamides: sulphonylurea compounds such as chlorsulfuron, chlorimuron, ethamethsulfuron, metsulfuron, primisulfuron, prosulfuron, triasulfuron, cinosulfuron, trifusulfuron, oxasulfuron, bensulfuron, tribenuron, ACC 322140, fluzasulfuron, ethoxysulfuron, fluzadsulfuron, nicosulfuron, rimsulfuron, thifensulfuron, pyrazosulfuron, clopyrasulfuron, NC 330, azimsulfuron, imazosulfuron, sulfosulfuron, amidosulfuron, flupyrsulfuron, CGA 362622 imidazolinones such as imazamethabenz, imazaquin, imazamethypyr, imazethapyr, imazapyr and imazamox; triazolopyrimidines such as DE 511, flumetsulam and chloransulam; dimethoxypyrimidines such as, for example, pyrithiobac, pyriminobac, bispyribac and pyribenzoxim.

+++ Tolerance to diclofop-methyl, fluazifop-P-butyl, haloxyfop-P-methyl, haloxyfop-P-ethyl, quizalafop-P-ethyl, clodinafop-propargyl, fenoxaprop-ethyl, tepraloxydim, alloxydim, sethoxydim, cycloxydim, cloproxydim, tralkoxydim, butoxydim, caloxydim, clefoxydim, clethodim.

&&& chloroacetanilides such as, for example, alachlor, acetochlor, dimethenamid

/// Protox inhibitors: for example diphenyl ethers such as, for example, acifluorfen, aclonifen, bifenox, chlornitrofen, ethoxyfen, fluoroglycofen, fomesafen, lactofen, oxyfluorfen; imides such as, for example, azafenidin, carfentrazone-ethyl, cinidon-ethyl, flumiclorac-pentyl, flumioxazin, fluthiacet-methyl, oxadiargyl, oxadiazon, pentoxazone, sulfentrazone, imides and other compounds such as, for example, flumipropyn, flupropacil, nipyraclofen and thidiazimin; and also fluazola and pyraflufen-ethyl.

TABLE 4

List of examples of transgenic plants having modified properties:

| Transgenic plants | Transgenically modified properties |
|---|---|
| *Dianthus caryophyllus* (carnation) line 66 [Florigene Pty. Ltd.] | Longer-lasting as a result of reduced ethylene accumulation owing to the expression of ACC synthase; tolerant to sulphonylurea herbicides |
| *Dianthus caryophyllus* (carnation) lines 4, 11, 15, 16 [Florigene Pty. Ltd.] | Modified flower colour; tolerant to sulphonylurea herbicides |
| *Dianthus caryophyllus* (carnation) lines 959A, 988A, 1226A, 1351A, 1363A, 1400A [Florigene Pty. Ltd.] | Modified flower colour; tolerant to sulphonylurea herbicides |
| *Brassica napus* (Argentine oilseed rape) lines 23-18-17, 23-198 [Monsanto Company] | Modified fatty acid content in the seeds |
| *Zea mays* L. (maize) lines REN-ØØØ38-3 (LY038) [Monsanto Company] | Elevated lysine content |
| *Zea mays* L. (maize) lines REN-ØØØ38-3, MON-ØØ81Ø-6 (MON-ØØ81Ø-6 x LY038) [Monsanto Company] | Elevated lysine content, corn borer resistant |
| *Cucumis melo* (melon) lines A, B [Agritope Inc.] | Delayed maturity as a result of the expression of S-adenosylmethionine hydrolase |
| *Carica papaya* (papaya) lines 55-1/63-1 [Cornell University] | Resistant to the papaya ring spot virus (PRSV) |
| *Solanum tuberosum* L. (potato) lines RBMT21-129, RBMT21-350, RBMT22-082 [Monsanto Company] | Resistant to the Colorado beetle and the potato leaf roll virus (PLRV) |
| *Solanum tuberosum* L. (potato) lines RBMT15-101, SEMT15-02, SEMT15-15 [Monsanto Company] | Resistant to the Colorado beetle and the potato virus Y (PVY) |
| *Glycine max* L. (soya bean) lines DD-Ø26ØØ5-3 (G94-1, G94-19, G168 [DuPont Canada Agricultural Products] | Modified fatty acid content in the seeds, in particular elevated oleic acid content |
| *Glycine max* L. (soya bean) lines OT96-15 [Agriculture & Agri-Food Canada] | Modified fatty acid content in the seeds, in particular reduced linolenic acid content |
| *Cucurbita pepo* (pumpkin) line ZW20 [Upjohn (USA); Seminis Vegetable Inc. (Canada)] | Resistant to viral infections, watermelon mosaic virus (WMV) 2 and zucchini yellow mosaic virus (ZYMV) |
| *Cucurbita pepo* (pumpkin) line CZW-3 [Asgrow (USA); Seminis Vegetable Inc. (Canada)] | Resistance to viral infections, cucumber mosaic virus (CMV), watermelon mosaic virus (WMV) 2 and zucchini yellow mosaic virus (ZYMV) |
| *Nicotiana tabacum* L. (tobacco) line Vector 21-41 [Vector Tobacco] | Reduced nicotine content |
| *Lycopersicon esculentum* (tomato) line 1345-4 [DNA Plant Technology] | Longer lasting as a result of reduced ethylene accumulation owing to the expression of ACC synthase |

TABLE 4-continued

| List of examples of transgenic plants having modified properties: | |
|---|---|
| Transgenic plants | Transgenically modified properties |
| *Lycopersicon esculentum* (tomato) line 35 1 N [Agritope Inc.] | Delayed maturity as a result of the expression of S-adenosylmethionine hydrolase |
| *Lycopersicon esculentum* (tomato) line CGN-89322-3 (8338) [Monsanto Company] | Delayed maturity as a result of the expression of ACCd |
| *Lycopersicon esculentum* (tomato) lines B, Da, F [Zeneca Seeds] | Delayed softening as a result of a reduced expression of polygalacturonase |
| *Lycopersicon esculentum* (tomato) line CGN-89564-2 (FLAVR SAVR) [Calgene Inc.] | Delayed softening as a result of a reduced expression of polygalacturonase |

The invention claimed is:

1. A method for improving the production potential of a transgenic maize, cotton, or soybean plant, comprising treating the transgenic plant with an effective amount of a mixture of (A) at least one compound of formula I

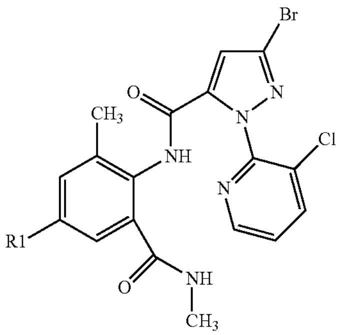

(I)

where R1 represents chlorine or cyano, and (B) at least one compound selected from the group consisting of imidacloprid, thiodicarb, clothianidin, methiocarb, thiacloprid, fipronil, tefluthrin, beta-cyfluthrin, and spinosad wherein the ratio of the compound of formula I to the compound of component (B) is in a range of 250:1 to 1:50.

2. A method according to claim 1, wherein said mixture comprises at least one compound of formula I and at least one compound of component (B), and a further active co-component.

3. A method according to claim 1, wherein the transgenic plant expresses *Bacillus thuringiensis* toxin and has at least one genetically modified structure or a tolerance according to the table:

| Transgenic plant | Feature of the plant/tolerance to |
|---|---|
| Maize | Lepidoptera, Coleoptera, Diptera, nematodes, armyworms, Western corn rootworm, *Sesamia* sp., *Aprotis ipsilon*, Asian corn borer, or weevils |
| Wheat | Lepidoptera, Coleoptera, Diptera, or nematodes |
| Barley | Lepidoptera, Coleoptera, Diptera, or nematodes |
| Rice | Lepidoptera, Coleoptera, or Diptera |
| Soya bean | Lepidoptera, Coleoptera, or aphids |
| Potato | Coleoptera or aphids |
| Tomato | Lepidoptera, whitefly, or aphids |

-continued

| Transgenic plant | Feature of the plant/tolerance to |
|---|---|
| Bell Pepper | Lepidoptera, whitefly, or aphids |
| Grapevines | Lepidoptera or aphids |
| Oilseed rape | Lepidoptera or aphids |
| *Brassica* vegetables | Lepidoptera or aphids |
| Pomaceous fruit | Lepidoptera, aphids, or mites |
| Melon | Lepidoptera, aphids, or mites |
| Banana | Lepidoptera, aphids, mites, or nematodes |
| Cotton | Lepidoptera, aphids, mites, nematodes, or whitefly |
| Sugar cane | Lepidoptera, aphids, mites, nematodes, whitefly, or beetles |
| Sunflower | Lepidoptera, aphids, mites, nematodes, whitefly, or beetles |
| Sugar beet or turnips | Lepidoptera, aphids, mites, nematodes, whitefly, beetles, or root-flies. |

4. A method according to claim 1, wherein the transgenic plant is transgenic cotton, rice, *Brassica*, potatoes, tomatoes, pumpkin, soya beans, maize, wheat, pome fruit, stone fruit, or citrus fruit having at least one modified principle of action according to the table:

| Principle | Tolerance to |
|---|---|
| acetolactate synthase | sulphonylurea compounds, imidazolinones, triazolopyrimidines, dimethoxypyrimidines, and/or N-acylsulphonamides |
| acetyl-CoA carboxylase | diclofop-methyl, fluazifop-P-butyl, haloxyfop-P-methyl, haloxyfop-P-ethyl, quizalafop-P-ethyl, clodinafop-propargyl, fenoxaprop-ethyl, tepraloxydim, alloxydim, sethoxydim, cycloxydim, cloproxydim, tralkoxydim, butoxydim, caloxydim, clefoxydim, and/or clethodim |
| hydroxyphenylpyruvate dioxygenase | isoxaflutole, isoxachlortole, sulcotrione, and/or mesotrione |
| nitrilase | bromoxynil and/or loxynil |
| inhibition of protein synthesis | chloroactanilides |
| hormone imitation | 2,4-D and/or mecoprop-P |
| protoporphyrinogen oxidase | Protox inhibitors |
| 5-enolpyruvyl-3-phosphoshikimate synthase | glyphosate and/or sulphosate |
| glutamine synthetase | gluphosinate and/or bialaphos. |

5. A method according to claim 1, wherein the transgenic plant is a transgenic plant according to Table 4.

6. A method according to claim 1, wherein the transgenic plant contains at least one genetic modification according to Table 2.

7. A method according to claim 1, wherein the transgenic plant contains at least one gene or a gene fragment coding for a Bt toxin.

8. A method according claim 1, wherein the mixture of at least one compound of the formula I and at least one compound of component (B) are used for controlling insects from the order Isoptera, Thysanoptera, Homoptera, Heteroptera, Lepidoptera, Coleoptera, Hymenoptera or Diptera.

9. A method according claim 1, wherein an application rate from 0.1 g/ha to 5.0 kg/ha is employed.

10. A plant part of a transgenic plant, wherein said plant part is obtainable by a method according to claim 1.

11. A plant part of a transgenic plant, wherein said plant part has been treated by a method according claim 1.

12. A method of claim 1, wherein an application rate from 0.1 to 500 g/ha is employed.

13. A method of claim 1, wherein an application rate from 10 to 500 g/ha is employed.

14. A method of claim 1, wherein an application rate from 10 to 200 g/ha is employed.

15. A plant part of claim 10 which comprises seed and/or propagation material.

16. A plant part of claim 11, which comprises seed and/or propagation material.

17. A method of claim 1, wherein a ratio of at least one compound of formula I to at least one compound of component (B) is in a range of 25:1 to 1:25.

18. A method of claim 1, wherein component (B) is imidacloprid or clothianidin.

* * * * *